United States Patent [19]

Mrozik et al.

[11] Patent Number: 5,830,875
[45] Date of Patent: Nov. 3, 1998

[54] 24-AND 25-SUBSTITUTED AVERMECTIN AND MILBEMYCIN DERIVATIVES

[75] Inventors: Helmut Mrozik, Matawan; Thomas L. Shih, Edison, both of N.J.

[73] Assignee: Merck & Co., Inc., Rahway, N.J.

[21] Appl. No.: 429,919

[22] Filed: Oct. 30, 1989

[51] Int. Cl.$^6$ .................. A61K 31/70; A61K 31/335; C07D 300/00; C07H 17/08
[52] U.S. Cl. ........................ 514/30; 514/450; 536/7.1; 549/264
[58] Field of Search ............... 536/7.1; 549/264; 514/30, 450

[56] References Cited

U.S. PATENT DOCUMENTS

| | | | |
|---|---|---|---|
| 3,950,360 | 4/1976 | Aoki et al. | 260/343.2 R |
| 4,171,314 | 10/1979 | Chabala et al. | 260/343.41 |
| 4,173,571 | 11/1979 | Chabala et al. | 260/343.41 |
| 4,199,569 | 4/1980 | Chabala et al. | 514/30 |
| 4,206,205 | 6/1980 | Mrozik et al. | 514/30 |
| 4,289,760 | 9/1981 | Mrozik et al. | 514/30 |
| 4,310,519 | 1/1982 | Albers-Schonberg et al. | 514/30 |
| 4,427,663 | 1/1984 | Mrozik et al. | 514/30 |
| 4,806,527 | 2/1989 | Christensen et al. | 514/30 |
| 4,849,446 | 7/1989 | Asato et al. | 514/450 |
| 4,916,120 | 4/1990 | Röben et al. | 514/30 |

FOREIGN PATENT DOCUMENTS

| | | |
|---|---|---|
| 79283/87 | 9/1987 | Australia . |
| 55140/90 | 5/1990 | Australia . |
| 170006 | 2/1986 | European Pat. Off. . |
| 214731 | 3/1987 | European Pat. Off. . |
| 242052 | 10/1987 | European Pat. Off. . |
| 262384 | 4/1988 | European Pat. Off. . |
| 264576 | 4/1988 | European Pat. Off. . |
| 276131 | 7/1988 | European Pat. Off. . |
| 290928 | 9/1988 | European Pat. Off. . |
| 319142 | 6/1989 | European Pat. Off. . |
| 2166436 | 5/1986 | United Kingdom . |

OTHER PUBLICATIONS

Chen et al (I) *Abstr. Pep. Am. Chem. Soc.* 1986 Meet MBTD 28 (1983).
Chen et al (II) *Arch Biochen Biophys* 269 pp. 544–547 (1989).
Schulman et al (I) *J. Antibiot.* 38 pp. 1494–1498 (1985).
Schulman et al (II) *Antimicrobial Agents and Chemotherapy* 31 pp. 744–747 (1987).
Fisher et al *Macrolide Antibiotics* Omura (Ed) Academic Press New York pp. 553–606 (1984).
Davies et al *Nat. Prod. Rep.* 3 pp. 87–121 (1986).
Shih, et al *Tetrahedron Letters* 31 pp. 3529–3532 (1990).
Shih, et al *Tetrahedron Letters* 31 pp. 3525–3528 (1990).

*Primary Examiner*—Elli Peselev
*Attorney, Agent, or Firm*—David L. Rose; Joseph F. DiPrima

[57] ABSTRACT

Novel avermectin and milbemycin derivatives are disclosed, where the C-24 and C-25 carbon atoms are substituted by hydrogen, alkyl, alkenyl, substituted alkyl or substituted alkenyl groups. These compounds can be further substituted at the 4"-, 5-, 13-, and 23-positions. The new C-24 and C-25 substituted avermect prepared by cleavage of known and suitably protected avermectin and milbemycin compounds. The new compounds are potent anti-parasitic agents, in particular, the compounds are anthelmintic, insecticidal and acaricidal agents.

4 Claims, No Drawings

24-AND 25-SUBSTITUTED AVERMECTIN AND MILBEMYCIN DERIVATIVES

BACKGROUND OF THE INVENTION

The term avermectin (previously referred to as C-076) is used to describe a series of compounds isolated from the fermentation broth of an avermectin producing strain of *Streptomyces avermitilis* and derivatives thereof. The morphological characteristics of the culture are completely described in U.S. Pat. No. 4,310,519. The avermectin compounds are a series of macrolides, each of which is substituted at the 13 position with a 4-(α-L-oleandrosyl)-α-L-oleandrose group. The avermectin compounds and the instant derivatives thereof have a very high degree of anthelmintic and anti-parasitic activity.

The avermectin series of compounds isolated from the fermentation broth have the following structure:

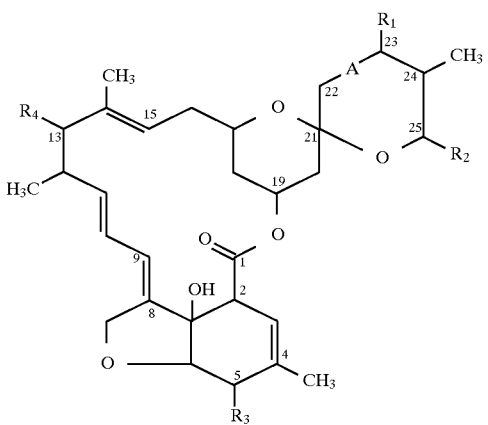

wherein $R_4$ is the 4'-(α-L-oleandrosyl)-α-L-oleandrosyloxy group of the structure:

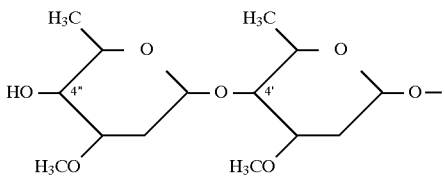

and wherein A at the 22,23 position indicates a single or a double bond; $R_1$ is a hydrogen or hydroxy and is present only when A indicates a single bond;

$R_2$ is iso-propyl or sec-butyl; and $R_3$ is methoxy or hydroxy

There are eight different avermectin natural product compounds and they are given the designations A1a, A1b, A2a, A2b, B1a, B1b, B2a, and B2b based upon the structure of the individual compounds.

In the foregoing structural formula, the individual avermectin compounds are as set forth below. (The R group is 4'-(α-L-oleandrosyl)-α-L-oleandrosyloxy:

| | (A) | $R_1$ | $R_2$ | $R_3$ |
|---|---|---|---|---|
| A1a | double bond | | sec-butyl | —OCH$_3$ |
| A1b | double bond | | iso-propyl | —OCH$_3$ |
| A2a | single bond | —OH | sec-butyl | —OCH$_3$ |
| A2b | single bond | —OH | iso-propyl | —OCH$_3$ |
| B1a | double bond | | sec-butyl | —OH |
| B1b | double bond | | iso-propyl | —OH |
| B2a | single bond | —OH | sec-butyl | —OH |
| B2b | single bond | —OH | iso-propyl | —OH |

The avermectin compounds are generaly isolated as mixtures of a and b components. Such compounds differ only in the nature of the $R_2$ substituent and the minor structural differences have been found to have very little effect on the isolation procedures, chemical reactivity and biological activity of such compounds.

In addition to these natural avermectins containing the 25-iso-propyl or 25-sec-butyl-substituent, closely related derivatives containing other branched or cyclic 25-alkyl or 25-alkenyl substituents, optionally further substituted by heteroatoms such as oxygen, sulfur, nitrogen, and halogen, are known in the literature. These derivatives are obtained through various adjustments and additions to the fermentation procedures as described fully in the European Patent Application 0 214 731.

Avermectins are products of microbial fermentations using the actinomycete *Streptomyces avermitilis*. These microbes use acetates and propionates as building blocks for most of the avermectin carbon chain, which is then further modified by microbial enzymes to give the completed avermectin molecules. It is known, however, that the carbon C-25 and the 2-propyl and 2-butyl substituents at this carbon are not derived from acetate or propionate units, but are derived from aminoacids L-valine and L-isoleucine, respectively. It was reasoned, that these aminoacids are deaminated to the corresponding 2-ketoacids, and that these then are decarboxylated to give 2-methylpropionic and 2-methylbutyric acids. These acids then have been found to be directly incorporated into the avermectin structures to give the 2-propyl and 2-butyl C-25 substituents, as is reported by Chen et al., *Abstr. Pap. Am. Chem. Soc.* (186 Meet.,MBTD 28, 1983).

It was also disclosed in European Patent Application 0 214 731 that additions of large amounts of other acids such as cyclopentanoic, cyclobutyric, 2-methylpentanoic, 2-methylhexanoic, thiophene-3-carboxylic acids and others to the fermentation broth of *S. avermitilis* cause the microbes to accept these acids as substitutes and to make small amounts of avermectins containing these acids in form of new C-25 substituents. Examples of such new avermectin derivatives are:

25-(thien-3-yl)-25-de-(1-methylpropyl)avermectin A2a
25-(cyclohex-3-enyl)-25-de-(1-methylpropyl)avermectin A2a
25-cyclohexyl-25-de-(1-methylpropyl)avermectin A2a
25-(1-methylthioethyl)-25-de-(1-methylpropyl)avermectin A2a
25-(2-methylcyclopropyl)-25-de-(1-methylpropyl) avermectin A2a Similar experiments producing avermectins "c" and "d" containing as C-25 substituents a 2-pentyl and 2-hexyl group are described by T. S. Chen et al. in *Arch. Biochem. Biophys.* 1989, 269, 544–547.

Still additional avermectin derivatives are produced through artifical modification of the fermentation of *Streptomyces avermitilis* either by addition of metabolic inhibitors such as sinefungin (as described by Schulman et al., *J.*

*Antibiot.* 1985, 38, 1494–1498) or by mutation of the parent strain (as described by Schulman et al., *Antimicrobial Agents and Chemotherapy*, 1987, 31, 744–747, and by EP-276-131-A to Pfizer INC.). Some of these avermectin derivatives are still further modified and are missing one or two of the 3'- and 3"-O-methyl groups (Schulman et al., J. Antibiot. 1985, 38, 1494–1498). Examples for such derivatives are:

3',3"-Bisdesmethylavermectin B1a and B1b
3',3"-Bisdesmethylavermectin B2a and B2b
3"-Desmethylavermectin B1a and B1b
3"-Desmethylavermectin B2a and B2b
3',3"-Bisdesmethyl-25-cyclohexyl-25-de-(2-butyl)-avermectin B2a
3',3"-Bisdesmethyl-25-cyclopentyl-25-de-(2-butyl)-avermectin B2a
3',3"-Bisdesmethyl-25-(3-thienyl)-25-de-(2-butyl)-avermectin B2a
3',3"-Bisdesmethyl-25-(3-furyl)-25-de-(2-butyl)-avermectin B2a
3',3"-Bisdesmethyl-25- (1 -methylthioethyl)-25-de-(2-butyl)-avermectin B1a.

Milbemycin compounds are similar to the above avermectin compounds in that the 16-membered macrocyclic ring is present. However, such compounds are unsubstituted at the 13-position and have a methyl or ethyl group at the 25 position (the position the $R_2$ group is found in the above structure). Such milbemycin compounds and the fermentation conditions used to prepare them are described in U.S. Pat. No. 3,950,360. In addition, 13-deoxy-avermectin aglycones are prepared synthetically from the avermectin natural products and are disclosed in U.S. Pat. Nos. 4,171,134 and 4,173,571. Such compounds are very similar to the milbemycins differing from some of the milbemycins in having an isopropyl or sec-butyl rather than a methyl or ethyl group at the 25-position. Still other milbemycin type structures are natural products described in Eur. Pat. App. 170,006 and U. K. Pat. App. 2,166,436 and are named LL-F28249 Antibiotic Complex or Antibiotics S541 or nemadectin. These are distinguished from the milbemycins and 13-deoxyavermectin aglycones by having a C-25 alkyl substituent containing an unsaturation.

The fermentation products have been chemically modified in order to obtain further antiparasitic and insecticidal analogs with improved properties such as potency, safety, antiparasitic spectrum, solubilities, stabilities and application forms. Publications of such procedures in the scientific and patent literature have been reviewed by Fisher, M. H.; Mrozik, H. In *Macrolide Antibiotics;* Omura, S., Ed.; Academic: New York, 1984; pp 553–606, and by Davies, H. G.; Green, R. H. *Nat. Prod. Rep.,* 1986, 3, 87–121.

For example, a group of semisynthetic avermectin derivatives were obtained by hydrogenating specifically the 22,23-double bond of avermectin B1 giving 22,23-dihydroavermectin B1 derivatives which have very potent anthelmintic and antiparasitic properties with a suffucient safety margin to allow mass application to humans infected with the filarial parasite causing the tropical disease onchocerciasis or "River Blindness". Another group of semisynthetic 10,11-dihydro avermectin B1 derivatives have longer persistent activities as agricultural miticides and insecticides due to increased photostability. Still other examples of semisynthetic avermectin derivatives contain a 8,9-oxide group, a 4a-hydroxy or acyloxy group, a 23-keto group, which all are potent antiparasitic and insecticidal compounds. It has also been described by Mrozik in U.S. Pat. No. 4,427,663 that amino substituents at the 4"- and 4'-positions have very high antiparasitic and insecticidal activities.

These compounds may be used as starting materials for the compounds of the instant invention without further modification, or when containing additional reactive groups, which are not to be modified under the reaction conditions applied, only after protection of such with a suitable protecting group.

SUMMARY OF THE INVENTION

The instant invention is concerned with derivatives of avermectin and nilbemycin compounds wherein the C-24 and C-25 carbon atoms are substituted by hydrogen, alkyl, alkenyl, substituted alkyl, substituted alkenyl, phenyl, substituted phenyl or heterocyclic groups. These compounds can be further substituted at the 4"-, 5-, 13-, and 23-positions. Thus it is the object of this invention to describe such compounds. It is a further object of this invention to describe the processes useful for the preparation of such compounds. A still further object is to describe the use of such compounds as anthelmintic, insecticidal, and acaricidal agents. Still further objects will become apparent from the reading of the following description.

DESCRIPTION OF THE INVENTION

The compounds of the instant invention have the following structural formula:

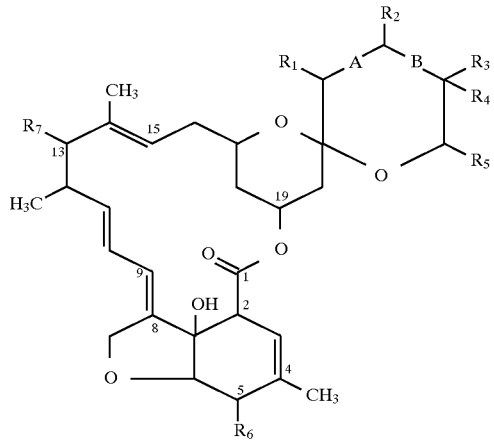

where A and B are single or double bonds, provided that only one of A and B is a double bond at any one time;

$R_1$=H, OH, loweralkanoyloxy, oxo, or halogen, when A is a single bond;

or:

$R_1$ is absent when A is a double bond;

$R_2$=OCO-lower alkyl or OSi-tri-lower alkyd, provided one of A or B is a double bond;

or:

$R_2$=H, OH, oxo, =NOH, =NOCH$_3$ or halogen, provided $R_1$ is OH and A and B are single bonds;

$R_3$=H, lower alkyl, cycloloweralkyl, or loweralkoxyloweralkyl;

$R_4$=H, lower alkyl, OH, OCO-loweralkyl, O-loweralkyl or halogen, provided A is a single or double bond and B is a single bond;

$R_5$=H, phenyl, optionally substituted phenyl wherein the substituents are from 1 to 3 of loweralkyl, loweralkoxy, halogen, amino, or loweralkanoylamino, heteroaryl such as pyrrolyl, pyridyl, or optionally substituted pyrrolyl, pyridyl wherein the substituents are from 1 to 3 of loweralkyl, loweralkoxy, halogen, amino, or loweralkanoylamino;

or:

$R_5$=H, $CH_3$, $C_2H_5$, a $C_3$–$C_{12}$ straight or branched alkyl, alkenyl, alkynyl, loweralkoxyalkyl or loweralkylthioalkyl group; a $C_3$–$C_8$ cycloalkyl or $C_5$–$C_8$ cycloalkenyl group, either of which may optionally be substituted by methylene or one or more $C_1$–$C_4$ alkyl groups or halo atoms; a $C_5$–$C_8$ cycloalkyl substituted $C_1$–$C_4$ alkyl group; or a 3 to 6 membered oxygen or sulfur containing heterocyclic ring which may be saturated, or fully or partly unsaturated and which may optionally be substituted by one or more $C_1$–$C_4$ alkyl groups or halogen atoms, furyl or thienyl groups; provided neither $R_3$ or $R_4$ are methyl groups;

$R_6$ is hydroxy, loweralkyloxy, oxo, or oxime;

$R_7$ is hydrogen, hydroxy, loweralkoxy, loweralkanoyloxy, oxymethyleneoxyloweralkylloweralkoxy, halogen or

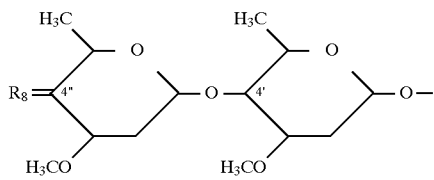

OR

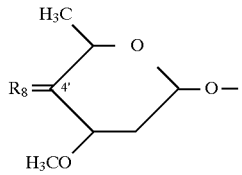

wherein $R_8$ is attached to C-4" or C-4' by a single bond and is hydroxy, loweralkanoyloxy, loweralkoxy, amino, N-loweralkylamino, N,N-diloweralkylamino, N-loweralkanoylamino, N-loweralkyl N-loweralkanoylamino; or $R_8$ is attached to C-4" or C-4' by a double bond and is oxo, semicarbazido, N-loweralkylsemicarbazido, N,N-diloweralkylsemicarbazido, loweralkanoylhydrazido, benzoylhydrazido, or loweralkylbenzoylhydrazido.

Preferred compounds of the instant invention are realized in the foregoing structural formula wherein A=single or double bond;

B=single bond;

$R_1$=H, or OH, provided A is a single bond;

or:

$R_1$ is absent when A is a double bond;

$R_2$=H, OH, oxo, =NOH, =$NOCH_3$ or halogen, provided A is a single bond and neither $R_3$ nor $R_4$ are methyl;

or:

$R_2$=OH, oxo, =NOH, =$NOCH_3$ or halogen, provided A is a single bond and $R_1$ is hydroxy;

$R_3$=H, lower alkyl, cycloloweralkyl, or loweralkoxyloweralkyl;

R4=H, or lower alkyl;

$R_5$=H, phenyl, optionally substituted phenyl wherin the substituent is loweralkyl, loweralkoxy, halogen, amino or loweralkanoylamino, heteroaryl such as pyrrolyl, pyridyl, or optionally substituted pyrrolyl, pyridyl wherin the substituent is loweralkyl, loweralkoxy, halogen, amino or loweralkanoylamino;

or:

$R_5$=H, $CH_3$, $C_2H_5$, a $C_3$–$C_{12}$ straight or branched alkyl, alkenyl, alkoxyalkyl or alkylthioalkyl group; a $C_3$–$C_8$ cycloalkyl or $C_5$–$C_8$ cycloalkenyl group, either of which may optionally be substituted by one or more $C_1$–$C_4$ alkyl groups or halogen atoms; a $C_5$–$C_8$ cycloalkyl substituted $C_1$–$C_4$ alkyl group, provided neither $R_3$ or $R_4$ are methyl groups;

$R_6$ is hydroxy;

$R_7$ is hydrogen, hydroxy, loweralkoxy, loweralkanoyloxy, oxymethyleneoxyloweralkylloweralkoxy, halogen or

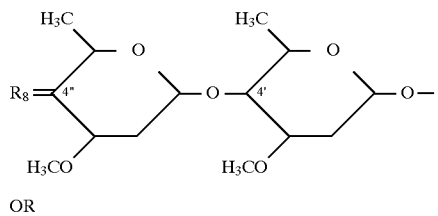

OR

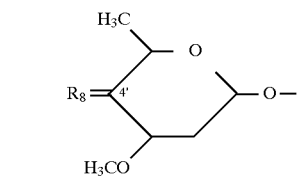

wherein $R_8$ is attached to C-4" or C-4' by a single bond and is hydroxy, loweralkanoyloxy, loweralkoxy, amino, N-loweralkylamino, N,N-diloweralkylamino, N-loweralkanoylamino, N-loweralkyl-N-loweralkanoylamino;

or $R_8$ is attached to C-4" or C-4' by a double bond and is oxo, semicarbazido, N-loweralkylsemicarbazido, N,N-diloweralkylsemicarbazido, loweralkanoylhydrazido, benzoylhydrazido, or loweralkylbenzoylhydrazido.

The most preferred compounds are realized in the foregoing structural formula wherein A at the 22,23 position represents a single bond and wherein $R_1$ is hydrogen, or A represents a double bond and $R_1$ is absent;

$R_2$=H, OH, oxo, =NOCH3, provided neither $R_3$ nor $R_4$ are methyl;

$R_3$=H or lower alkyl;

$R_4$=H or lower alkyl;

$R_5$=H, phenyl, or substituted phenyl, wherin the substituent is loweralkyl, loweralkoxy, halogen, amino or loweralkanoylamino or:

$R_5$=H, $CH_3$, $C_2H_5$, a $C_3$–$C_{12}$ straight or branched alkyl, alkenyl, loweralkoxyalkyl or loweralkylthioalkyl group; a $C_3$–$C_8$ cycloalkyl or $C_5$–$C_8$ cycloalkenyl group, provided neither $R_3$ or $R_4$ are methyl groups;

$R_6$ is hydroxy;

$R_7$ is hydrogen, hydroxy, loweralkoxy, loweralkanoyloxy, oxymethyleneoxyloweralkylloweralkoxy or

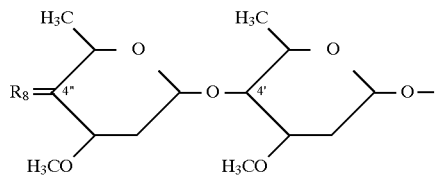

-continued

[Chemical structure with OR, H₃C, R₈=C-4', H₃CO, O, O—]

wherein R₈ is attached to C-4" or C-4' by a single bond and is hydroxy, loweralkanoyloxy, loweralkoxy, amino, N-loweralkylamino, N,N-diloweralkylamino, N-loweralkanoylamino, N-loweralkyl—N-loweralkanoylamino;

or R₈ is attached to C-4" or C-4' by a double bond and is oxo.

Preferred compounds of the instant invention are further realized in the following compounds:

24-demethyl-25-de(2-butyl)avermectin B1a
24-demethyl-25-de(2-butyl)-22,23-dihydro-22-hydroxyavermectin B1a
24-demethyl-25-de(2-butyl)-22,23-dihydroavermectin B1a
24-demethyl-25-de(2-butyl)-25-phenylavermectin B1a
24-demethylavermectin B1a
24-demethyl-25-epiavermectin B1a
25-de(2-butyl)avermectin B1a
24-epi-25-de(2-butyl)avermectin B1a
24-demethyl-25-de(2-butyl)-25-cyclopentylavermectin B1a
24-demethyl-25-de(2-butyl)-25-cyclopentyl-25-epiavermectin B1a
24-demethyl-25-de(2-butyl)-25-cyclohexylavermectin B1a
24-demethyl-25-de(2-butyl)-25-octylavermectin B1a
24-demethyl-25-de(2-butyl)-25-methylavermectin B1a
24-demethyl-25-de(2-butyl)-25-ethylavermectin B1a
25-de(2-butyl)-25-methylavermectin B1a
25-de(2-butyl)-25-ethylavermectin B1a
24-demethyl-24-ethoxy-25-de(2-butyl)avermectin B1a
24-methyl-25-de(2-butyl)avermectin B1a
24-demethyl-25-de(2-butyl)-25-phenylavermectin B1a monosaccharide
24-demethyl-25-de(2-butyl)-25-phenylavermectin B1a aglycone
24-demethyl-25-de(2-butyl)-22,23-dihydro-25-phenylavermectin B1a
24-demethyl-25-de(2-butyl)-13-deoxy-22,23-dihydro-25-phenylavermectin B1a aglycone
24-demethyl-25-de(2-butyl)-13-deoxy-13-fluoro-22,23-dihydro-25-phenylavermectin B1a aglycone
24-demethyl-25-de(2-butyl)-13-O-(2-methoxyethoxymethyl)-22,23-dihydro-25-phenylavermectin B1a aglycone 24-demethyl-25-de(2-butyl)-25-(2-thienyl)avermectin B1a
24-demethyl-25-de(2-butyl)-25-(4-pyridyl)avermectin B1a 25-de(2-butyl)-25-phenylavermectin B1a
24-demethyl-24-ethyl-25-de(2-butyl)-25-phenylavermectin B1a 25-de(2-butyl)-25-(4-methoxyphenyl)avermectin B1a
25-de(2-butyl)-25-(3,5-dichlorophenyl)avermectin B1a
25-de(2-butyl)-25-(4-acetylaminophenyl)avermectin B1a
24-demethyl-25-de(2-butyl)-25-benzylavermectin B1a
25-de(2-butyl)-25-benzylavermectin B1a 4"-deoxy-4"-epi-acetylamino-24-demethyl-25-de(2-butyl)-25-cyclopentylavermectin B1a
4"-deoxy-4"-epi-acetylamino-24-demethyl-25-de(2-butyl)avermectin $B_{1a}$
4"-deoxy-4"-acetylamino-24-demethyl-25-de(2-butyl)-22,23-dihydroavermectin $B_{1a}$
25-de(2-butyl)-25-phenyl-4"-deoxy-4"-epi-methylaminoavermectin $B_{1a}$ In the instant invention the term "loweralkyl" is intended to indicate those alkyl groups of from 1 to 6 carbon atoms such as methyl, ethyl, propyl, isopropyl, butyl, pentyl, hexyl, and the like.

The term "loweralkoxy" is intended to include those alkoxy groups of from 1 to 6 carbon atoms such as methoxy, ethoxy, propoxy, isopropoxy, butoxy, pentoxy, hexoxy, and the like.

The term "loweralkanoyl" is intended to include those alkanoyl groups of from 1 to 6 carbon atoms such as formyl, acetyl, propionyl, butyryl, pentanoyl, hexanoyl, and the like.

The term "halogen" is intended to include the halogen atoms, fluorine, chlorine, bromine, or iodine.

The above structural formula is shown without a definitive stereochemistry. However, during the course of the synthetic procedures used to prepare such compounds, the products of such procedures can be a mixture of stereoisomers. In particular, the substituents of the stereoisomers at the 4"-, 4'-, 13-, 23-, 24-, and 25-positions may be oriented either α- or β- representing such groups being below or above the general plane of the molecule, respectively. In each such case both the α- and β- configurations are intended to be included within the ambit of this invention. In certain cases the term "epi" is used to distinguish the stereoisomer being of opposite configuration to the natural compound at one specific asymmetrical carbon atom.

Chemical intermediates and starting materials for the compounds described above are also new and are claimed as part of this invention. They have the structures depicted below:

[Chemical structure showing avermectin-type macrocyclic structure with labeled positions 1, 2, 4, 5, 8, 9, 13, 15, 19, CH₃ groups, OH, O—R, R₆, R₇]

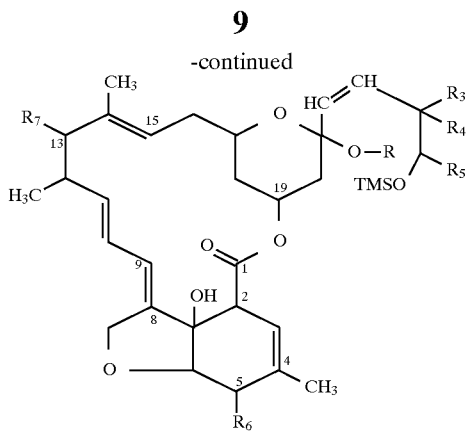

-continued where R is lower alkyl and the substituents $R_3$, $R_4$, $R_5$, $R_6$, $R_7$, and $R_8$ are as stated above.

PREPARATION OF STARTING MATERIALS

The ultimate starting materials for the compounds of this invention are the avermectin and milbemycin fermentation products described in the Background of the Invention, in particular those containing a 23-oxo substituent or a group such as a hydroxy, which can be readily oxidized to the required intermediate. Avermectin B2a (Compound I of Scheme 1, below, showing also some compounds as partial structures of carbon atoms numbered 17 and higher) is a particularly useful and readily available fermentation product for this purpose, but others are not excluded for this reaction series. Its oxidation to the 23-oxo analog is descibed in U.S. Pat. No. 4,289,760. For this purpose the 4"- and 5-hydroxy groups are protected as trialkylsilylethers, advantagiously as the 4",5-di-O-tert-butyldimethylsilylether. This is oxidized using the well known Swern oxidation conditions employing oxalyl chloride-dimethylsulfoxide followed by triethylamine as reagents, but other oxidants may also be employed. The 23-oxo group is ready for transformation into the silylenolether required for the cleavage of the bond between carbon 22 and 23. Reaction of the such protected 23-ketone (Scheme 1: compound II) with trimethylsilyl chloride in the presence of a strong base gives the desired 23-O-trimethylsilyl-22,23-en-23-ol ether derivative and simultaneously puts a trimethylsilyl group onto the tertiary C-7 hydroxy group (Scheme 1: compound III). The selection of the base for this reaction is of crucial importance, since it is well known that strong bases readily epimerize the 2-position and rearrange the 3,4-double bond to give analogs of low biological potency. It was found surprisingly that from a selection of numerous bases lithium bis (trimethylsilyl)amide is capable to form the desired silyl enol ether without any further side reactions. It was now discovered that the newly formed 22,23-double bond of the trimethylsilyl enol ether reacted selectively in the presence of four additional double bonds with a peroxy acid such as 3-chloroperoxybenzoic acid to form a 22,23-oxide intermediate (Scheme 1: compound IV), which spontaneously rearranged to form the 22-hydroxy-23-oxo derivative (Scheme 1: compound V). The 22,23-carbon bond of this intermediate could now be cleaved using lead tetraacetate as oxidating reagent to afford an intermediate where the C-22 is oxidized to an aldehyde and C-23 to a carboxylic acid (Scheme 1: compound VI). This acid is still attached to C-21 of the macrolide ring through an acetal oxygen atom. Transacetalization in methanol with pyridinium tosylate as acid catalyst cleaves this bond and gives a C-21 epimeric mixture of an avermectin derivative which has lost carbon atoms 23 to 28, and has a methoxy and an aldehyde group attached to carbon atom 21 (Scheme 1: compounds VIIA and VIIB).

SCHEME 1:
PREPARATION OF STARTING MATERIALS

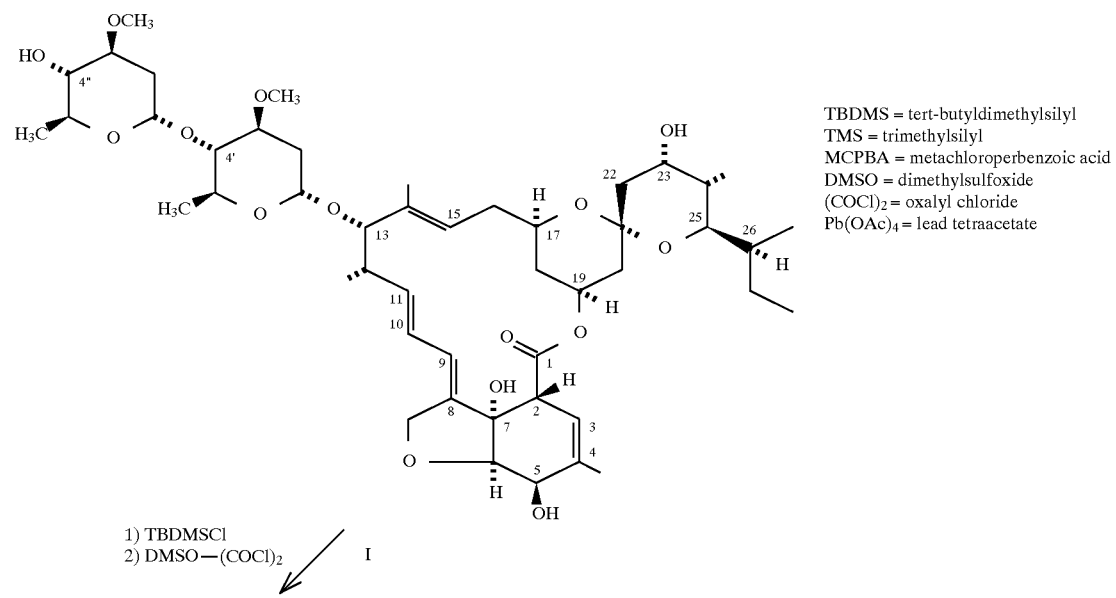

TBDMS = tert-butyldimethylsilyl
TMS = trimethylsilyl
MCPBA = metachloroperbenzoic acid
DMSO = dimethylsulfoxide
$(COCl)_2$ = oxalyl chloride
$Pb(OAc)_4$ = lead tetraacetate -continued
SCHEME 1:
PREPARATION OF STARTING MATERIALS

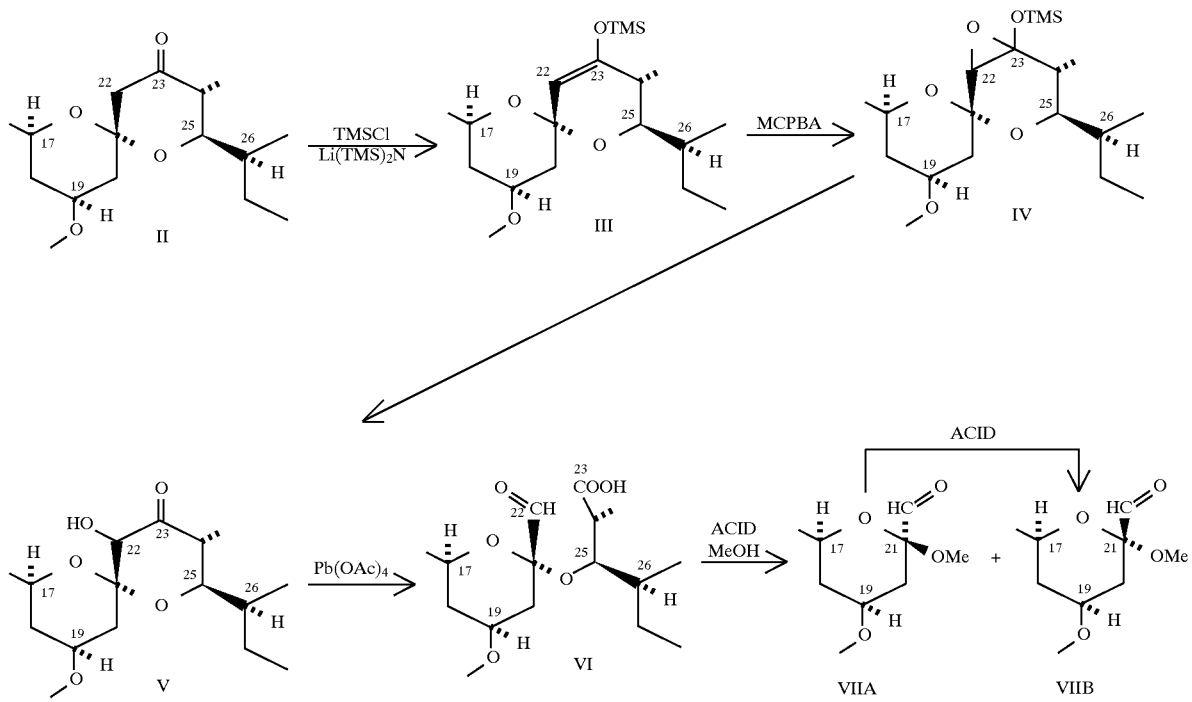

PREPARATION OF COMPOUNDS

Having this crucial intermediate in hand (Scheme 3: compounds VIIA and VIIB, showing only partial structures of carbon atoms numbered 17 and higher), we are now in a position to add carbon synthons to the C-22 aldehyde carbon atom. These synthons contain a protected hydroxy group at the appropriate position where they can react (after deprotection) with the C-21 carbon atom in order to complete the dioxaspirane ring and yield new avermectin analogs with novel substitutions at the 24 and 25 position. To this end the aldehyde is reacted with a triphenyl phosphonium salt in a Wittig reaction. Again the choice of base for this reaction is important due to the base sensitivity of the avermectins, and potassium bis(trimethylsilyl)amide was found to be the preferred base. The thus formed olefinic intermediate containing the double bond in the 22,23-position (avermectin numbering) and a trimethylsilyl protected hydroxygroup at the 25-position (Scheme 3: compounds VIIIa and VIIIB) is now treated with pyridinium tosylate in anhydrous methanol, which accomplishes first the cleavage of the C-25-O-trimethylsilyl ether and then the transketalisation to form the dioxaspirane structure. Removal of the 4"-,5-, and 7-O-protecting groups either with hydrofluoric acid-pyridine-tetrahydrofuran or with p-toluenesulfonic acid in methanol gives the desired products of this invention (Scheme 3: compound IX).

The required phosphonium salts are obtained routinely by starting for instance with the readily available (S)-3-chloro-1-phenyl-1-propanol, converting it to the corresponding 3-iodo derivative (with sodium iodide in methylethyl ketone), protecting the hydroxy group as a trimethylsilyl ether (with bis(trimethylsilyl)trifluoroacetamide), which then is reacted with triphenylphosphine to the required phosphonium iodide (Scheme 2). If the required substituted propanols are not available, they can be prepared from readily available 2-substituted acroleins, where the 2-substituent corresponds to the eventual C-24 substituent of the avermectins. Hydrochloric acid addition to the double bond and reaction of the chloroaldehyde with a Grignard reagent RMgX, where R provides the eventual C-25 substituent of the avermectins and X is a halogen radical, provides the variously substituted chloropropanols (Scheme 2). Other substituted propanols are prepared from 2-substituted malonate esters as further described in the experimental section.

A reaction sequence as described above for avermectin B2a can also be carried out with

SCHEME 2:
PREPARATION OF C-23 SYNTHONS

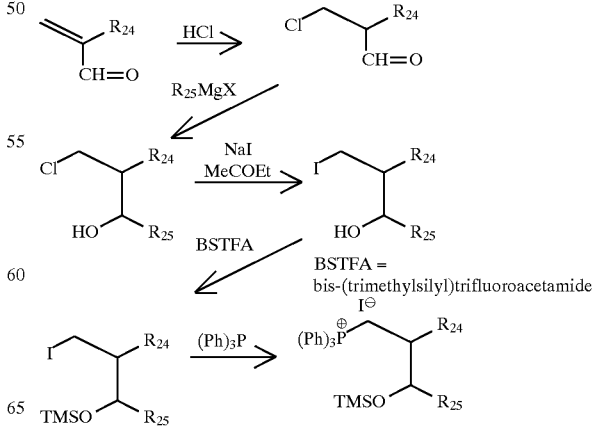

SCHEME 3:
PREPARATION OF COMPOUNDS

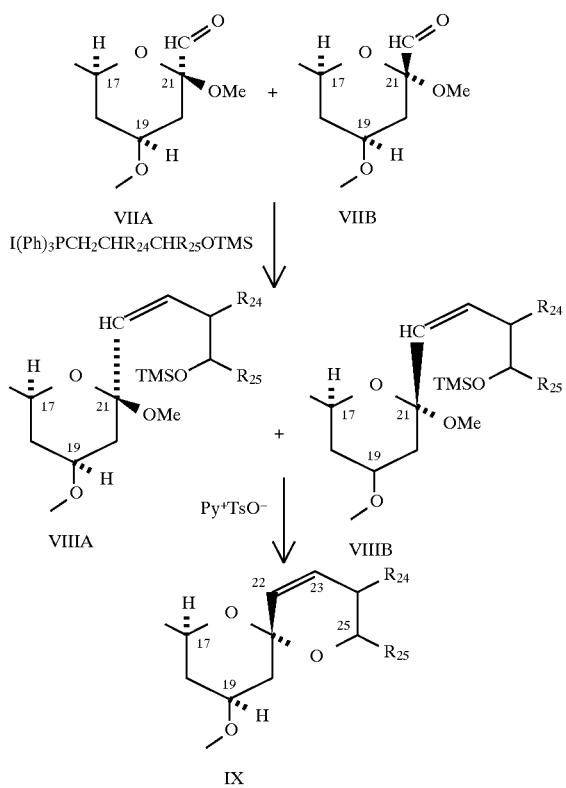

starting materials having as C-13 substituents a monooleandroside, a suitably protected hydroxy group, a hydrogen, halogen, alkoxy, alkanoyloxy or alkyl group, and products obtained by this variation of the above procedure all also meant to be included in the ambit of this invention.

The products obtained through the reaction sequence described above can be used as starting materials for further modifications in order to improve potency, safety, anthelmintic and insectcidal spectrum, stability, application formulations and other desirable properties for antiparasitic agents.

Additional reaction sequencies may be required to prepare further compounds for the instant invention. Specifically, reactions are carried out at the 4", 4', 5, 13, 22, and 23-positions. Thus oxidation of the 4"- or 4'-hydroxy group, reductive amination of the thus produced 4"- or 4'-oxo to the 4"- or 4'-amino compounds and their subsequent acylation is fully described in U.S. Pat. No. 4,427,663.

During the oxidation and certain substitution reactions described above it may be necessary to protect the 5-hydroxy group to avoid oxidation or substitution at that position. With this position protected reactions at the 4"- or 4'-positions may be carried out without affecting the remainder of the molecule. Subsequent to any of the above described reactions the protecting group may be removed and the unprotected product isolated. The protecting group employed is ideally one which may be readily synthesized, will not be affected by the reactions at the 4"- and 4'-positions and may be removed without affecting any other functionality of the molecule. One preferred type of protecting group for the avermectin type of molecule is the tri-substitiuted silyl group, preferably the trialkyl silyl group. One especially preferred example is the t-butyldimethylsilyl group. The reaction preparing the protected compound is carried out by reacting the hydroxy compound with the appropriately substituted silylhalide, preferably the silylchloride in an aprotic polar solvent such as methylene chloride, benzene, toluene, ethyl acetate, tetrahydrofuran, dimethylformamide and the like. In order to minimize side reactions, there is included in the reaction mixture a base to react with the acid halide released during the course of the reaction. Preferred amines are imidazole, pyridine, or triethylamine. The base is required in amounts equimolar to the amount of hydrogen halide liberated; however, generally several equivalents of the amine are employed. The reaction is stirred at from 0° C. to the reflux temperature of the reaction mixture and is complete in from ½ to 16 hours. The silyl group is removed by stirring the silylated compound in methanol catalized by an acid preferably a sulfonic acid monohydrate such as p-toluenestilfonic acid monohydrate. The reaction is complete in about 1 to 12 hours at from 0° to 50° C. Alternatively, the silyl group may be removed by treatment of the silyl compound with anhydrous pyridine-hydrogen fluoride in tetrahydrofuran. The reaction is complete in from 3 to 24 hours at from 0° to 25° C.

Another useful modification of products obtained in the above reaction sequence are analogs in which the 22,23-double bond has been reduced to a single bond. The preferred catalyst for the selective hydrogenation of the 22,23-double bond is one having the formula:

$$[((R)_3P)_3RhY]$$

wherein R is loweralkyl, phenyl, or loweralkyl substituted phenyl and Y is halogen. The reduction is completely described in U.S. Pat. No. 4,199,569.

Other intermediates which are either used in the above reaction scheme or are prepared from the products of the above described reaction sequence involve the preparation of the monosaccharide. The processes which may be used to prepare the monosaccharide derivatives of the avermectin compounds are described in U.S. Pat. No. 4,206,205. The reaction consists generally in treating the starting disaccharide with acid in an aqueous organic solvent mixture. Water concentration of from 0.1 to 20% by volume and acid concentrations of from about 0.01 to 0.1% will predominantly produce the monosaccharide, while acid concentrations from 1 to 10 % produce the aglycones. Another procedure for the preparation of the monosaccharide utilizes a 1% mineral acid solution in isopropanol at 20° to 40° C. for from 6 to 24 hours. Mineral acids such as sulfuric, phosphoric, and the like may be employed.

The substituent at the 25-position of the avermecins is inert to the reaction conditions and the presence of alkyl groups, alkenyl groups, cycloalkyl groups, cycloalkenyl groups, aryl groups and the like at this position will have little affect on further chemical modifications of the avermectins.

All of the foregoing reactions carried out at the 4"-position of the avermectin can be carried out at the 4'-position of the monosaccharide to afford the correspondingly substituted monosaccharide derivatives.

BIOLOGICAL ACTIVITIES OF THE INSTANT COMPOUNDS

The novel compounds of this invention have significant parasiticidal activity as anthelmintics, ectoparasiticides, insecticides, and acaracides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, and poultry. Among the helminths the group of worms described as nematodes causes widespread and oftentimes serious infection in various species of animals. The most common genera of nematodes infecting the animals referred to above are Haemonchus, Trichostronigylus, Ostertagia, Nematodirus, Cooperia, Ascaris, Bunostomum, Oesophagostomum, Chabertia, Trichuris, Strongylus, Trichonema, Dictocaulus, Capillaria, Heterakis, Toxocara, Ascaridia, Oxvuris, Ancylostoma, Uncinaria, Toxascaris, and Parascaris. Certain of these, such as Nematodirus, Cooperia, and Oesophagostomum attack primarily the intestinal tract while others, such as Haemonchus and Ostertagia, are more prevalent in the stomach while still others such as Dictocaulus are found in the lungs. Still other parasites may be located in other tisues and organs of the body such as the heart and blood vessels, subcutaneous and lymphatic tissue and the like. The parasitic infections known as helminthiasis lead to anemia, malnutrition, weakness, weight loss, severe damage to the walls of the intestinal tract and other tissues and organs and, if left untreated, may result in the death of the infected host. The avermectin compounds of this invention have unexpectedly high activity against Dirofilaria in dogs, Nematospiroides, Syphacia, Aspiculuris in rodents, anthropod ectoparasites of animals and birds such as ticks, mites, lice, fleas, blowfly, in sheep Lucilia sp., biting insects and such migrating dipterous larvea as Hypoderma sp. in cattle, Gastrophilus in horses, and Cuterebra sp. in rodents.

The instant compounds are also useful against parasites which infect humans. The most common genera of parasites of the gastro-intestinal tract of man are Ancvlostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracuncultis and extra-intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp, carpet beetle, Attagenus sp., and the housefly *Musca domestica*.

The compounds are also useful against insect pests of stored grains such as Tribolium sp., Tenebrio sp. and of agricultural plants such as spider mites (Tetranychus sp.) aphids (Acyrthiosiphon sp.); against migratory orthopterans such as locusts and immature stages of insects living on plant tissue. The compounds are useful as a nematocide for the control of soil nematodes and plant parasites such as Meloidogyne sp. which may be of importance in agriculture.

These compounds may be administered orally in a unit dosage form such as a capsule, bolus or tablet, or as a liguid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 5% by weight of the active compound. Preferred drench formulations may contain from 0.01 to 0.1% by weight active compound. The capsules or boluses are comprised of the active ingredient admixed with a carrier vehicle such as starch, talc, magnesium stearate, or di-calcium phosphate.

Where it is desired to administer the avermectin derivatives in a dry, solid unit dosage form, capsules, boluses, or tablets containing the desired amount of active compound usually are employed. The dosage forms are prepared by intimately and uniformly mixing the active ingredients with suitable finely divided diluents, fillers, disintegrating agents, and/or binders such as starch, lactose, talc, magnesium stearate, vegetable gums and the like. Such unit dosage formulations may be varied widely with respect to their total weight and content of antiparasitic agent depending upon factors such as the type of host animal to be treated, the severity and type of the infection and the weight of the host.

When the active compound is to be admnistered via the animal feedstuff, it is intimately dispersed in the feed or used as a top dressing or in the form of pellets which may then be added to the finished feed or optionally fed separately. Alternatively, the antiparasitic compounds of our invention may be administered to the animals parenterally, for example, by intraruminal, intramuscular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil, and the like. Other parenteral vehicles such as organic preparations using solketal, glycerol formal, and aqueous parenteral formulations are also used. The active avermectin compound or compounds are dissolve or suspended in the parenteral formulation for administration; such formultions generally contain from 0.005 to 5% by weight of the active compound.

Although the antiparasitic agents of this invention find their primary use in the treatment and/or prevention of helminthiasis,they are also useful in the prevention and treatment of diseases caused by other parasites, for example, arthropod parasites such as ticks, lice, fleas, mites, and other biting insects in domesticated animals and poultry. They are also effective in treatment of parasitic diseases that occur in other animals including humans. The optimum amount to be employed for the best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1–5 days. With the preferred compounds of the invention, excellent control of such parasites is obtained in animals by administratering from about 0.025 to 0.5 mg per kg of body weight in a single dose. Repeaat treatments are given as required to combat re-infections and are dependent upon the species of parasite and the husbandry techniques being employed. The techniques for administering these materials to animals are known to those skilled in the veterinary field. When the compounds described herein are administered as a component of the feed of the animals, or dissolved or suspended in the drinking water, compositions are povided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for the direct feeding to the animal or for addition to the feed either directly or after an intermediate dilution or blending step. Typical carriers or diluents suitable for such compositions include, for example, distillers' dried grains, corn meal, citrus meal, fermentaion residues, ground oyster shells, wheat shorts, molasses solubles, corn cob meal, edible bean mill feed, soya grits, crushed limestone and the like. The active avermectin compounds are intimately dispersed throughout the carrier by methods such as grinding, stirring, milling, or tumbling. Compositions containing from about 0.005 to 2.0% weight of the active compound are particularly suitable as feed premixes. Feed supplements, which are fed directly to the animal, contain from about 0.002 to 0.3% by weight of the active compounds.

Such supplements are added to the animal feed in an amount to give the finished feed the concentration of active compound desired for the treatment and control of parasitic diseases. Although the desired concentration of the active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

In using the compounds of this invention, the individual avermectin components may be prepared and used in that form. Alternatively, mixtures of two or more of the indivdual avermectin components may be used, or other active compounds not related to the compounds of this invention.

The compounds of this invention are also useful in combatting agricultural pests that inflict damage upon crops while they are growing or in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

The avermectin derivatives prepared in the folowing examples are generally isolated as amorphous solids and not as crystalline solids. They are thus characterized analytically using techniques such as mass spectrometry, nuclear magnetic resonance spectrometry and the like. Being amorphous, the compounds are not characterized by sharp melting points, however, the chromatographic and analytical methods employed indicate that the compounds are pure.

EXAMPLE 1

4",5-Di-O-t-Butyldimethylsilyl-Avermectin B2a

To a solution of 58.2 g (65 mmol) of dried avermectin B2a in 400 mL of sieve-dried dimethylformamide and 30 mL of freshly distilled triethylamine was added a solution of 29.8 g (198 mmol, 3 equiv.) of t-butyldimethylsilyl chloride in 200 mL of dichloromethane. The mixture was stirred at room temperature 16 h then poured into ice water and extracted with dichloromethane. The organic phases were combined and washed with water, brine, and dried over magnesium sulfate. Evaporation of the solvent afforded an oil which was purified by silica gel high performance liquid chromatography using 20% ethyl acetate-hexane to yield 34.2 g of 4",5-Di-O-t-butyldimethylsilylavermectin B2a characterized by its NMR and mass spectra.

EXAMPLE 2

4",5-Di-O-t-Butyldimethylsilyl-23-oxo-Avermectin B2a

A 5-L 3-neck flask equipped with a thermometer, mechanical stirrer, and dropping funnel was charged with 400 mL of dichloromethane and 16 mL (0.185 mol) of oxalyl chloride. The solution was cooled to −70° C., under nitrogen while a solution of 25 mL (0.350 mol) of dimethylsulfoxide in 200 mL of dichloromethane was added dropwise over 30 min keeping the internal temperature below −65° C. The mixture was stirred at −70° C. for 1 h. A solution of 114.75 g (0.103 mol) of 4",5-diO-t-butyldimethylsilyl-avermectin B2a in 900 mL of dichloromethane was then added dropwise over 45 min keeping the temperature of the mixture below −65° C. After an additional 2 h at −70° C. 115 mL of triethylamine was added dropwise over 10 min again keeping the temperature below −65° C. The reaction was then stirred at approximately 10° C. for 1 h before the solvent was concentrated off in vacuo. The residue was taken up in 1.5 L of ether and washed with 500 mL of water. The aqueous layer was extracted with 500 mL of ether. The combined ether layers were washed sequentially with 2×1 L of water, 1 L of saturated sodium bicarbonate, and 1 L of brine, then dried over magnesium sulfate. The solvent was removed to afford 110 g of yellow foam purified by column chromatography (4 kg silica gel, eluted with 5–25% ethyl acetate-hexane eluant.). The product was obtained as a yellow foam (101 g, 88% yield). NMR (300 MHz, TMS) δ0.08 (d,J=6 Hz), 0.14 (s), 0.9 (s), 0.93 (s), 0.98 (m), 1.16 (d,J=7 Hz), 1.2 (d,J=7 Hz), 1.24 (d,J=7Hz), 1.45 (s), 1.5 (m), 1.8 (s), 2.22 (m), 2.44 (m), 3.12 (t,J=9 Hz), 3.2 (t,J=9 Hz), 3.32 (s), 3.42 (s), 3.6 (m), 3.81 (d,J=6 Hz), 3.93 (s), 3.98 (sh s), 4.44 (d,J=6 Hz), 4.62 (dq,J=2,14 Hz), 4.74 (d,J=3 Hz), 4.93 (t,J=7 Hz), 5.3 (m), 5.7 (m), 5.8 (m); mass spec: FAB 1123 (M+Li).

EXAMPLE 3

4",5-Di-O-t-Butyldimethylsilyl-7-O-trimethylsilyl-23-O-trimethylsilyloxy-Avermectin B1a To a solution of 101 mg (0.09 mmol) of 4"5-di-O-t-butyldimethylsilyl-23-oxo-avermectin B2a in 2 mL of distilled tetrahydrofuran at −78° C. was added 0.400 mL of a 1.0M solution of lithium bis(trimethylsilyl)amide in a mixture of hexanes. The mixture was stirred at −78° C., under argon, for 1 h before 0.20 mL of the supernatant of a centrifuged 1:3 mixture of triethylamine and trimethylchlorosilane was added dropwise via a syringe. After another 30 min, 2 ml of a saturated aqueous sodium bicarbonate solution was added and the mixture was allowed to warm to room temperature. The reaction mixture was then partitioned between water and ether and the ethereal extracts were combine and dried over magnesium sulfate. Filtration and evaporation of the ether afforded 120 mg of 4",5-di-O-t-butyldimethylsilyl-7-O-trimethylsilyl-23-O-trimethylsilyloxy-avermectin B1a characterized by its NMR δ0.08 (d,J=6 Hz), 0.12 (s), 0.18 (s), 0.88 (s), 0.92 (s), 1.18 (d,J=8 Hz), 1.23 (d,J=8 Hz), 1.26 (d,J=8 Hz), 1.5 (s), 1.51 (m), 1.78 (s), 2.3 (m) 2.58 (m), 3.12 (t,J=9 Hz), 3.22 (t,J=9 Hz), 3.25 (s), 3.32 (s), 3.4 (s), 3.8 (d,J=6 Hz), 3.82 (m), 3.98 (s), 4.39 (d,J=4 Hz), 4.6 (q,J=16 Hz), 4.68 (sh d,J=2 Hz, C22H), 4.8 (d,J=3 Hz), 4.9 (m), 5.1 (m), 5.25 (d,J=3 Hz), 5.45 (s), 5.7 (m).

EXAMPLE 4

4",5-Di-O-t-Butyldimethylsilyl-7-O-Trimethylsilyl-22-Hydroxy-23-Oxo-Avermectin B2a To a solution of 135 mg (0.107 mmol) of 4",5-Di-O-t-butyldimethylsilyl-7-O -trimethylsilyl-23-O-trimethylsilyl-Avermectin B1a in 2 mL of dichloromethane was added a solution of 21 mg (0.12 mmol) of m-chloroperbenzoic acid in 1 mL of dichloromethane in one portion. After 20 min at 20° C., 0.2 mL of dimethyl sulfide was added to react with any peracid. The mixture was stirred another 30 min before the addition of aqueous sodium bicarbonate and extraction with ethyl acetate. The combined organic fractions were dried, filtered, and evaporated to afford 150 mg of solid. This product mixture was separated by preparative thin layer chromatography (20% ethyl acetate-hexane) to afford 40 mg of 4",5-Di-O-t-butyldimethylsilyl-7-O-trimethylsilyl-22-hydroxy-23-oxo-Avermectin B2a. NMR δ0.08 (d,J=6 Hz), 0.14 (s), 0.88 (s), 0.92 (s), 0.96 (d,J=6 Hz), 0.98 (d,J=6 Hz), 1.16 (d,J=7 Hz), 1.20 (d,J=6 Hz), 1.23 (d,J=6 Hz), 1.43 (s), 1.50 (s), 1.52 (m), 1.78 (s), 2.24 (m), 2.4 (dd,J=6,12 Hz), 2.58 (m), 3.12 (t,J=9 Hz), 3.22 (t,J=9 Hz), 3.3 (s), 3.32 (s), 3.4 (s), 3.62 (m), 3.82 (m), 3.82 (d,J=6 Hz), 3.92 (d,J=7 Hz), 3.97 (s), 4.38 (d,J=3 Hz), 4.6 (q,J=15 Hz), 4.77 (d,J=3 Hz), 4.83 (m), 5.05 (br d,J=7 Hz), 5.25 (d,J=3 Hz), 5.5 (s), 5.7 (m); mass spec. FAB 1212 (M+Li+H).

EXAMPLE 5

Preparation of aldehyde-acid (Compound VI, Scheme 1)

To a solution of 600 mg (0.5 mmol) of 4",5-Di-O-t-butyldimethylsilyl-7-O -trimethylsilyl-22-hydroxy-23-oxo-Avermectin B2a in 6 mL of benzene in an aluminum foil-covered glass vial was added 400 mg (0.9 mmol) of lead tetraacetate in one portion. After 30 min at 20° C., the solution was poured into a separatory funnel containing 12 mL of water and 600 mg of sodium sulfite. The mixture was then shaken and extracted with ethyl acetate. The combined extracts were dried (MgSO$_4$), filtered, and evaporated to afford 600 mg of solid. Flash chromatography through a column of silica gel eluting with 2:1 hexane:ethyl acetate, then acetone afforded 250 mg of starting material and 230 mg of aldehyde VI. NMR δ0.08 (d,J=6 Hz), 0.13 (s), 0.89 (s), 0.92 (s), 1.15 (d,J=6 Hz), 1.18 (d,J=6 Hz), 1.20 (d,J=6 Hz), 1.26 (d,J=6 Hz), 1.5 (s), 1.53 (m), 1.78 (s), 2.3 (m), 2.78 (br s), 3.13 (t,J=9 Hz), 3.23 (t,J=9 Hz), 3.23 (s), 3.32 (s), 3.36 (m), 3.42 (br s), 3.68 (m), 3.81 (m), 3.82 (d,J=6 Hz), 3.98 (s), 4.38(s), 4.6 (q,J=15 Hz), 4.79 (d,J=2 Hz), 4.86 (br s), 5.12 (br s), 5.3 (s), 5.44 (s), 5.7 (m).

EXAMPLE 6

Transketalization of Aldehyde VI to Aldehydes VIIA and VIIB (Scheme 1) and 2R,3R,4S-2,4-dimethyl-3-hydroxyhexanoic acid To a solution of 8 g of pyridinium tosylate in 80 mL of dry methanol was added 16.3 g of aldehyde VI from Example 5. The mixture was stirred at 20° C. for 1.5 h before 4 mL of triethylamine was added. The mixture was then transferred to a separatory funnel containing 4.4 g of sodium bicarbonate and 500 mL of water. The mixture was extracted with ether and the aqueous layer was then acidified with 2N HCl and extracted with ethyl acetate to recover 1.4 g of 2R,3R,4S-2,4-dimethyl-3-hydroxyhexanoic acid as an amber oil. The ether extracts were combined and dried over magnesium sulfate. Filtration and evaporation of the solvent afforded 15.5 g of solid as a 1:1:1 mixture of methoxy ketals VIIA and VIIB and aldehyde-acid VI, in addition to some minor products with a slower Rf than VIIB but faster than VI (isomer VIIB which has lost some silyl groups). The mixture was separated by flash column chromatography on 550 g of silica gel eluted with 3:1 and then 2:1 hexane:ethyl acetate to yield 5.1 g VIIA, 4.0 g VIIB, and 3.9 g VI, each characterized by NMR and mass spectroscopy. NMR of VIIA: δ0.08 (d,J=6 Hz), 0.12 (s), 0.14(s), 0.88 (s), 0.92 9s), 1.17 (d,J=7 Hz), 1.21 (d,J=7 Hz), 1.25 (d,J=7 Hz), 1.5 (m), 1.51 (s), 1.78 (s), 2.3 (m), 2.5(m), 3.13 (t,J=9 Hz), 3.22 (t,J=9 Hz), 3.28(sh d, J=2 Hz), 3.32 (s), 3.38 (s), 3.44 (s), 3.65 (m), 3.82 (d,J=6 Hz), 3.98 (s), 4.38 (d,J=3 Hz), 4.6 (dq,J=2,15 Hz), 4.7 (m), 4.78 (d,J=3 Hz), 5.12 (d,J=11 Hz), 5.30 (d,J=3 Hz), 5.48 (s), 5.57 (m), 5.75 (dd,J=11,16 Hz), 9.37 (s). NMR of VIIB: δ0.08 (d,J=6 Hz), 0.13 (s), 0.88 (s), 0.90 (m), 0.92 (s), 1.18 (d,J=7 Hz), 1.21 (d,J=7 Hz), 1.26 (d,J=6 Hz), 1.42 (s), 1.5 (m), 1.52 (s), 1.6 (m), 1.78(s), 1.90 (d,J=12 Hz), 2.35 (m), 2.58 (tt,J=6,2 Hz), 3.13 (t,J=9 Hz), 3.22(t,J=9 Hz), 3.25 (s), 3.28 (s), 3.32 (s), 3.43(s), 3.66(m), 3.82 (d,J=6 Hz), 3.84 (m), 3.99(s), 4.38 (d,J=3 Hz), 4.60 (dq,J=2,15 Hz), 4.80 (d,J=3 Hz), 4.90 (m), 5.15 (dd,J=5,12 Hz), 5.29 (d,J=3 Hz), 5.46 (s), 5.57 (m,J=9 Hz), 5.63 (d,J=12 Hz), 5.76 (dd,J=12,15 Hz), 9.39 (s). The stereochemical assignment at C21 for isomers VIIA and VIIB was based on the nonreversible conversion of VIIA to VIIB when each pure isomer was resubjected to acidic methanol. Isomer VIIB being the thermodynamically stable isomer has been assigned the axial methoxyl/equitorial formyl configuration. The chiral acid was esterified with excess diazomethane and purified by flash chromatography with 15% ethyl acetate-hexane to yield 1 g of methyl ester [$^-$]$_D$=−9.5°, c=8.9 g/dL dichloromethane, characterized by its NMR spectrum.

EXAMPLE 7

4",5-Di-O-t-butyldimethylsilyl-7-O-trimethylsilyl-21,21-O-,22,23-bis-seco-24-demethyl-25-de(2-butyl)-25-O-t-butyldimethylsilys-21-methoxy-Avermectin 1a (Scheme 3 structure VIII, $R_{24}$=$R_{25}$=H)

To a mixture of 151 mg (0.275 mmol) of triphenyl-3-t-butyldimethylsilyloxypropyl phosphonium bromide in 1 mL of freshly distilled toluene under argon was added 0.44 mL (0.22 mmol) of a 0.5M toluene solution of potassium bis(trimethylsilyl)amide. The orange mixture was stirred at 20° C. for 30 min before cooling to -78° C. A solution of 202 mg (0.185 mmol) of aldehyde VIIA in 0.5 mL of toluene was added dropwise and the mixture was then allowed to warm to 20° C. After 1 h the reaction mixture was quenched with 10 mL of sodium bicarbonate solution and extracted with ethyl acetate. The extracts were combined and dried over MgSO$_4$, filtered and concentrated to afford 329 mg of solid. Purification by flash column chromatography with 10% ethyl acetate-hexane yielded 173 mg of cis-olefin adduct VIIIA. NMR δ0.06(s), 0.09(d,J=6 Hz), 0.13 (s), 0.14(s), 0.89 (s), 0.94(s), 1.18(d,J=7 Hz), 1.22(d,J=6 Hz), 1.26(d,J=6 Hz), 1.40(t,J=12 Hz),1.52(s), 1.78(s), 2.24–2.6(m), 3.13 (t,J=9 Hz), 3.22(t,J=9 Hz), 3.30(s), 3.33(s), 3.43(s), 3.6(m), 3.68 (t,J=7 Hz), 3.82 (d,J=6 Hz), 3.98(s), 4.38(d,J=3 Hz), 4.6(m), 4.6(dq,J=2,15 Hz), 4.80(d,J=3 Hz), 5.13(t,J=7 Hz), 5.30(d, J=3 Hz), 5.4(d,J=12 Hz), 5.5 (s), 5.5–5.9(m); C13 NMR (olefinic) 118, 120.3, 120.6, 125.1, 127.5, 134.57, 134.66, 135.4, 136.5, 140.5;mass spectra FAB 1255 (M+Li). The analogous reaction was run with aldehyde VIIB to afford a similar yield of adduct VIIIB: NMR δ0.04 (s), 0.08(d,J=6 Hz), 0.14(s), 0.87(s), 0.89(s), 0.94(s), 1.18(d,J=7 Hz), 1.21 (d,J=6 Hz), 1.26(d,J=6 Hz), 1.52 (s), 1.6(m), 1.78(s), 2.2–2.6 (m), 3.13(t,J=9 Hz), 3.14(s), 3.23(t,J=9 Hz), 3.26(s), 3.32(s), 3.33(m), 3.45(s), 3.63(t,J=6 Hz), 3.7(m), 3.82(d,J=6 Hz), 3.98 (s), 4.38(d,J=6 Hz), 4.6(dq,J=2,15 Hz), 4.82(d,J=3 Hz), 4.93(m,J=5 Hz), 5.15(dd,J=3,9 Hz), 5.29(d,J=12 Hz), 5.30 (d,J=3 Hz), 5.48–5.80(m); C13 NMR (olefinic) 118.4, 120.56, 120.67, 125.05, 131.00, 131.2, 134.36, 135.07, 136.56, 140.51.

EXAMPLE 8

4",5-Di-O-t-butyldimethylsilyl-7-O-trimethylsilyl-24-demethyl-25-de(2-butyl)-Avermectin B1a (Scheme 3 structure IX, $R_{24}$=$R_{25}$=H)

To a solution of 6.3 mg of pyridinium p-toluenesulfonate (PPTS) in 1.2 mL of sieve-dried methanol was added 18 mg of adduct VIIIA or VIIIB. After 2 days at 20° C., the methanol was removed in vacuo and the residue was taken up in dichloromethane and separated by preparative silica gel layer chromatography (PLC) to afford the identical product mixture from the two epimeric structures A and B: 10 mg of 4",5-diO-t-butyldimethylsilyl-7-O-trimethylsilyl-24-demethyl-25-de(2-butyl)-avermectin B1a and 5 mg of 4",5-di-O-t-butyldimethylsilyl-24-demethyl-25-de(2-butyl)-avermectin B1a characterized by their NMR and mass spectra.

EXAMPLE 9

24-Demethyl-25-de(2-butyl)-avermectin B1a

To a polypropylene vial containing 129 mg of a purified mixture of 4",5-di-O-t-butyldimethylsilyl-7-O-timethylsilyl-24-demethyl-25-de(2-butyl)-avermectin B1a and 4",5-di-O-t-butyldimethylsilyl-24-demethyl-25-de(2-butyl)-avermectin B1a obtained from the PPTS/methanol cyclization reaction was added 10 mL of hydrogen fluoride-pyridine in tetrahydrofuran (1:3:6 volume dilution of commercially available HF-pyridine complex: freshly distilled pyridine: THF). The anhydrous solution was stirred at 20° C. for 2 days before dilution with ether and removal of the HF with an aqueous sodium bicarbonate wash. The ethereal extracts were combined and dried over $MgSO_4$. The product was purified by flash chromatography on silica gel (56 mg): NMR (C13) 15.09, 17.66, 18.38, 19.90, 20.29, 24.41, 34.13, 34.22, 34.58, 36.49, 39.69, 40.16, 45.62, 56.36, 56.61, 57.78, 67.16, 67.66, 68.04, 68.17, 68.39, 76.01, 78.14, 79.04, 79.33, 80.22, 80.36, 81.33,94.59, 94.99, 98.46, 117.95, 118.12, 120.21, 124.72, 128.76, 129.03, 134.99, 137.88, 139.64, 173.59; mass spectra FAB 809 (M+Li).

EXAMPLE 10

Preparation of (R) or [(S)-3-Trimethylsilyloxy-2-methyl-propyl]triphenylphosphonium bromide Commercially available (R) or [(S)-3-hydroxy-2-methyl-propyl]triphenylphosphonium bromide was treated in dry N,N-dimethylformamide (DMF) with excess bis(trimethylsilyl)trifluoroacetamide (BSTFA) at room temperature over 12 h to silylate the hydroxyl function. The solvent was removed in vacuo and the residue recrystallized from ether-hexane or dried in a Kugelrohr oven at 75° C. overnight under vacuum. The degree of silylation was determined by NMR integration of the silyl protons in the final salts.

EXAMPLE 11

4",5-Di-O-t-butyldimethylsilyl-7-O-trimethylsilyl-21,21-O-,22,23-bis-seco-25-de(2-butyl)-25-O-trimethylsilyl-21-methoxy-Avermectin B1a (Scheme 3 structure VIII, $R_{24}=R_{25}=H$)

To a slurry of 355 mg (0.7 mmol) of [(S)-3-trimethylsilyloxy-2-methylpropyl]triphenylphosphonium bromide in 1.5 mL of toluene under argon was added 0.600 mL of a 0.5M solution of potassium bis(trimethylsilyl)amide in toluene. After 15 minutes at 20° C., the orange mixture was cooled to −78° C. before a solution of 305 mg (0.279 mmol) of aldehyde VIIA in 1 mL of toluene was added dropwise. Upon completion of addition of the aldehyde the cooling bath was removed and after 30 min the mixture was quenched with 5 mL of a solution of sodium bicarbonate. Extraction with ether and flash chromatographic separation of the mixture afforded 77 mg of product; NMR (select signals) δ1.02(d, J=7 Hz, C24 methyl), 3.30(s), 3.32(s), 3.42(s) (methoxys), 5.38(d,J=11 Hz, C21H);and 150 mg of recovered aldehyde VIIA. Use of the (R)-phosphonium salt gave the corresponding epimeric product at C24 of the Wittig adduct; NMR (select signals) δ1.01(d,J=7 Hz, C24 methyl), 3.31(s), 3.32(s), 3.41(s), 5.38(d,J=12 Hz, C21H).

EXAMPLE 12

4",5-Di-O-t-butyldimethylsilyl-7-O-trimethylsilyl-24-epi-25-de(2-butyl)-Avermectin B1a To a solution of 140 mg of PPTS in 2 mL of methanol was added 77 mg (0.062 mmol) of 4",5-di-O-t-butyldimethylsilyl-7-O-trimethylsilyl-21,21-O-,22,23-bis-seco-24-epi-25-de(2-butyl)-25-O-trimethylsilyl-21-methoxy-avermectin B1a. After 6 h at 20° C., the acid was neutralized with aqueous sodium bicarbonate and extracted with ether. PLC afforded 56 mg of a mixture of the title compound (NMR (select signals) δ1.08(d,J=7 Hz, C24 methyl), 3.32(s), 3.44(s), 2 methoxyls, 5.50(d,J=11 Hz, C22H), 5.92(dd,J=6,11 Hz, C23H)) and the desilylated 7-hydroxyl derivative characterized by their NMR and mass spectra.

EXAMPLE 13

25-De(2-butyl)-Avermecfin B1a

Following the procedure outlined in example 9, 92 mg of 4",5-di-O-t-butyldimethylsilyl -7-O-trimethylsilyl-21,21-O-,22,23-bis-seco-25-de(2-butyl)-25-O-trimethylsilyl-21-methoxy-avermectin B1a from example 11 was desilylated and spontaneously cyclized with 4 mL of HF-pyridine-THF to afford 20 mg of title compound: NMR (select signals) δ0.90(d,J=7 Hz, C24 methyl), 3.42(s), 3.46(s), 5.5.56(dd,J=3, 10 Hz,C22H), 5.80(d,J=10 Hz, C23H) and mass spec FAB 823 (M+Li).

EXAMPLE 14

24-Epi-25-de(2-butyl)-Avermectin B1a

Utilizing the procedure of example 11 and the (R)-phosphonium salt a similar Wittig condensation with aldehyde VIIA gave the required olefin which was cyclized to the spiroketal with PPTS in methanol. Desilylation as in example 9 gave the title compound: NMR (select signals) δ1.10(d,J=7 Hz, C24 methyl), 3.42(s), 3.46(s), methoxyls, 5.56(d,J=10 Hz, C22H), 5.97(dd,J=5,10 Hz, C23H) and mass spec FAB 823 (M+Li).

EXAMPLE 15

(S)-3-Iodo-1-phenyl-1-propanol

Commercially available (S)-3-chloro-1-phenyl-1-propanol (6 g) was heated with excess sodium iodide (4 equiv., 18 g) and a few drops of triethylamine in 30 mL of methyl ethyl ketone at 100° C. for 20 h. A sample was taken and monitored by NMR to determine the extent of conversion. The solvent was removed in vacuo and the residue was taken up in dichloromethane and filtered to remove the salts and the iodoalcohol was purified by flash chromatography to yield 6.9 g of product.

EXAMPLE 16

(S)-3-Iodo-1-phenyl-1-trimethylsilyloxypropane

The iodoalcohol obtained in example 15 was protected as the trimethylsilylether with either BSTFA in DMF or trimethylsilyltriflate and triethylamine in dichloromethane following standard procedures. For example, to 800 mg of iodoalcohol in 4 mL of dichloromethane was added 2 mL of triethylamine and 1.5 mL of trimethylsilyltriflate. After 30 min the solvent was removed in vacuo and the residue was flash chromatographed to afford 990 mg of product characterized by its NMR and mass spectra.

EXAMPLE 17

(S)-[(3-phenyl-3-trimethylsilyloxy)propyl] triphenylphosphonium iodide

A solution of 408 mg of iodophenylpropyltrimethylsilyl ether and 321 mg (1 equiv.) of triphenylphosphine in 5 mL of toluene and a drop of triethylamine was heated under nitrogen at 100° C. for 64 h. The toluene was removed in vacuo and the residue was triturated in ether-hexane to afford 500 mg of solid product characterized by its NMR and mass spectra.

EXAMPLE 18

General procedure for the preparation of 3-chloro-1-alkyl(aryl)-1-propanol

3-Chloropropanal prepared by addition of dry hydrogen chloride to distilled acrolein (Shriner at al., J. Org. Chem. 103–105, (1939)) is added to an excess of the appropriate Grignard reagent at 20° C. After 30 min the mixture is cooled with an acetone-dry ice bath and quenched with an aqueous ammonium chloride solution. The product is isolated by ether extraction and purified by silica gel chromatography.

EXAMPLE 19

[(3-alkyl(aryl)-3-trimethylsilyloxy)propyl] triphenylphosphonium iodide

The corresponding 3-chloro-1-alkyl(aryl)-1-propanol obtained in Example 18 is converted to the iodoalcohol by the procedure described in Example 15 and then protected as the trimethylsilylether as in Example 16. The corresponding phosphonium salt was prepared as outlined in Example 17. Following that protocol the following salts have been prepared and characterized:
(R,S)-[(3-cyclopentyl-3-trimethylsilyloxy)propyl] triphenylphosphonium iodide,
(R,S)-[(3-cyclohexyl-3-trimethylsilyloxy)propyl] triphenylphosphonium iodide,
[(3-(2-butyl)-3-trimethylsilyloxy)propyl] triphenylphosphonium iodide (diastereomeric mixture).

Starting with the appropriate 3-chloro-1-alkyl(aryl)-1-propanol following the procedure for the above cases, the following salts are obtained:
(R,S)-[(3-(benzyl)-3-trimethylsilyloxy)propyl] triphenylphosphonium iodide;
(R,S)-[(3-(3-furyl)-3-trimethylsilyloxy)propyl] triphenylphosphonium iodide;
(R,S)-[(3-(2-thienyl)-3-trimethylsilyloxy)propyl] triphenylphosphonium iodide;
(R,S)-[(3-(4-pyridyl)-3-trimethylsilyloxy)propyl] triphenylphosphonium iodide;
(R,S)-[(3-(1-octyl)-3-trimethylsilyloxy)propyl] triphenylphosphonium iodide;
(R,S)-[(3-(1-ethyl)-3-trimethylsilyloxy)propyl] triphenylphosphonium iodide.

EXAMPLE 20

(S) and (R)-[(3-trimethylsilyloxy)butyl] triphenylphosphonium iodide

Commercially available (S)-1,3-butanediol, 1.47 g, was dissolved in 10 mL of dichloromethane and 5 mL of triethylamine. To this was added 3.22 g of p-toluenesulfonyl chloride. After 1.5 h the primary monotosylate was purified by silica gel flash chromatography to afford 2.85 g of (S)-3-hydroxybutyl-1-p-tosylate. This was converted to 2.33 g of (S)-1-iodo-3-hydroxybutane by refluxing with 4.2 g of sodium iodide in 20 mL of acetone and 5 drops of triethylamine (17 h). The resulting iodoalcohol was silylated with bis(trimethylsilyl)trifluoroacetamide in dimethylformamide at room temperature. The corresponding (S)-[(3-trimethylsilyloxy)butyl]triphenylphosphonium iodide was prepared by heating the iodosilylether with an equivalent of triphenylphosphine in toluene 48 h at 100° C. Starting with the commercially available (R)-1,3-butanediol, the corresponding (R)-[(3-trimethylsilyloxy)butyl] triphenylphosphonium iodide is prepared and characterized by NMR and mass spectra.

EXAMPLE 21

[(2-Methyl-3-trimethylsilyloxy)butyl] triphenylphosphonium iodide

Commercially available 4-hydroxy-3-methyl-2-butanone, 10.4 g, (technical grade 65%) was reduced with excess lithium aluminum hydride (25 mL of a 1.0 M solution) in 50 mL of ether and worked up with the addition of 2 mL of ethyl acetate, 1 mL of water, 1 mL of 15% sodium hydroxide, and anhydrous sodium sulfate. The solid was extracted overnight in a Sohxlet extractor with 250 mL of refluxing ether. The ether was removed in vacuo and the diol was distilled in a Kugelrohr at 150° C., 12 torr to give 3.89 g of product. This 1,3-dihydroxy-2-methylbutane (as a mixture of diastereomers) was converted to the primary tosylate as in Example 20 and then to the iodoalcohol with sodium iodide. Subsequent silylation with bis(trimethylsilyl) trifluoroacetamide and treatment with triphenylphosphine in toluene gave the title phosphonium iodide (diastereoisomers) characterized by its NMR and mass spectra.

EXAMPLE 22

[(2-Methyl-3-trimethylsilyloxy)pentyl] triphenylphosphonium iodide

Commercially available 1-hydroxy-2-methyl-3-butene (1.91 g) was silylated with 5 g of t-butyldimethylsilyl chloride and 4.7 g of imidazole in 5 mL of DMF and 5 mL of dichloromethane for 3 h. The mixture was poured into water and extracted with 9:1 hexane:ether. The extracts were combined and concentrated to afford 4.3 g of 1-t-butyldimethylsilyloxy-2-methyl-3-butene which was used without further purification. The silyloxybutene and 3 mg of Sudan 7B red dye was dissolved in 50 mL of dichloromethane and treated at −78° C. with ozone until the red color was discharged. The solution was then warmed to room temperature for 30 min before cooling back to −78° C. A solution of 2.0M ethyl magnesium bromide (30 mL) in THF was added over 10 min and the resulting mixture was warmed to room temperature for 45 min before cautious addition of aqueous ammonium chloride at low temperature to quench the excess Grignard reagent. Extraction of the mixture with ether and evaporation of the solvent yielded 3.96 g residual oil confirmed by NMR to be the desired product. This was dissolved in 20 mL of methanol with 475 mg of p-toluenesulfonic acid monohydrate and stirred at 20° C. for 2 h. The methanol was then removed in vacuo and the residual product was flash chromatographed on 400 g of silica gel (1:1 hexane:ethyl acetate) to yield 1.1 g of 1,3- dihydroxy-2-methyl-pentane as a diastereomeric mixture (NMR). Subsequent conversion to the title phosphonium iodide was accomplished following the procedure set forth in examples 20 and 21.

EXAMPLE 23

(2R,3R,4S)-[(2,4-Dimethyl-3-trimethylsilyloxy, hexyl]triphenylphosphonium iodide.

The (2R,3R,4S)-2,4-dimethyl-3-hydroxyhexanoic acid methyl ester (1.3 g) from Example 6 was reduced to the corresponding diol with lithium aluminum hydride in ether at 0° C. for 1 h. Ether extraction from a dilute hydrochloric acid workup and concentration gave 680 mg of diol $[\alpha]_D$= +24.5°, c=13.1 g/dL dichloromethane. This diol was selectively monotosylated at the primary hydroxyl site with excess tosyl chloride, triethylamine, and dichloromethane to afford 1.08 g of chromatographically purified tosylate. Further conversion to the iodoalcohol with sodium iodide and acetone (60° C., 3 h) gave 902 mg of chromatographically purified product, $[\alpha]_D$=−12.6°, c=12.3 g/dL dichloromethane. The iodoalcohol (570 mg) was silylated with trimethylsilyltrifluoromethane sulfonate, triethylamine, and dichloromethane (1 h, 20° C.) and chromatographed to afford 610 mg of product: NMR δ0.16(s), 0.82(d,J=7 Hz), 0.91(t,J=6 Hz), 0.93(d,J=6 Hz), 1.0–1.6(m), 3.34(m, 3H). Final conversion to the phosphonium salt was acccomplished by heating with triphenylphosphine as in example 21 to afford 800 mg of solid product.

EXAMPLE 24

Preparation of Avermectin B1a

The phosphonium iodide from example 23 was condensed with aldehyde VIIB from example 6 following the reaction scheme outlined by examples 7–9 to afford avermectin B1a in 40% yield overall based on aldehyde VIIB. The product was identical in all respects to the natural product.

EXAMPLE 25

24-demethyl-25-de-(2-butyl)-25-phenylavermectin B1

A Wittig condensation of the ylid derived from (S)-[(3-phenyl-3-trimethylsilyloxy)propyl]triphenylphosphonium iodide (130 mg) of Example 17 with aldehyde VIIB gave the cis-olefin precursor (74 mg) which was cyclized to the spiroketal (90%) with PPTS and methanol. Removal of the silyl protecting groups with HF-pyridine-THF gave the title product (50%): NMR δ0.90(dd), 1.14(d,J=7 Hz), 1.24(d,J=6 Hz), 1.26(d,J=6 Hz), 1.42(s), 1.48(s), 1.5–1.75(m), 1.8(br d,J=11 Hz), 1.88(s), 2.3(m), 2.5(m), 3.14(t,J=9 Hz), 3.20(t, J=9 Hz), 3.30(sh d,J=2 Hz), 3.36(s), 3.40(s), 3.4–3.6(m), 3.76(m), 3.91(s), 3.95(d,J=6 Hz), 4.29(t,J=6 Hz), 4.68(AB, J=15 Hz), 4.76(d,J=3 Hz), 4.93(dd,J=3,9 Hz), 4.97(m,J=6 Hz), 5.36(d,J=3 Hz), 5.42(s), 5.50(m,J=6 Hz), 5.76(m), 6.06(m), 7.3–7.5(m) and mass spec 885 (M+Li).

EXAMPLE 26

24-Demethyl-25-de(2-butyl)-25-cyclopentylavermectin B1and 24-demethyl-25-de(2-butyl)-25-epicyclopentylavermectin B1

A Wittig condensation of 183 mg of (R,S)-[(3-cyclopentyl-3-trimethylsilyloxy) propyl] triphenylphosphonium iodide from Example 19 with 300 mg of aldehyde VIIB gave 283 mg of olefinic adduct. Cyclization of 153 mg of this adduct gave 52 mg of the normal C25 isomer and 61 mg of the epi-C25 isomer (separated by TLC). Each isomer was deprotected with HF-pyridine-THF to afford 21 mg of the title compound (NMR (select signals) δ4.11(s,C7OH), 5.40(s, C1"H and C3H), 5.42(m, C19H), 5.61(d,J=10 Hz, C22H), 5.97(m, C23H)) and 18 mg of the epi-C25 title compound (NMR (select signals) δ4.10(dt,J=3,11 Hz, C25H), 5.30(m, C19H), 5.39(d,J=3 Hz, C1"H), 5.44(s, C3H), 5.57(d,J=10 Hz, C22H), 5.94(m, C23H)) both with mass spec FAB of 877 (M+Li).

EXAMPLE 27

24-Demethylavermectin B1a and 24-demethyl-25-epiavermectin B1a

The Wittig condensation of 180 mg of [(3-(2-butyl)-3-trimethylsilyloxy)propyl]triphenylphosphonium iodide from example 19 with 300 mg of aldehyde VIIA following the procedure outlined in example 11 gave 259 mg of olefinic adduct. This was dissolved in 6 mL of methanol containing 60 mg of PPTS and the solution was stirred at 20° C. for 2 h. The methanol was then removed in vacuo and the residual solid was separated by PLC to afford 76 mg of 25-epi product and 97 mg of 25-normal product (faster eluting on TLC). These were separately desilylated to yield 24-demethylavermectin B1a, 29 mg; NMR (select signals) δ1.00(d,J=6 Hz, OH), 4.10(s, C7OH), 5.40(overlapped C3H and C1"H), 5.44(m, C19H), 5.61(d,J=10 Hz, C22H), 5.99 (m, C23H) and 24 mg of 24-demethyl-25-epiavermectin B1a; NMR (select signals) δ1.08(d,J=6 Hz, OH), 4.11 (dt, J=3,12 Hz, C25H), 5.32(m,C19H), 5.39(d,J=3 Hz, C1"H) 5.44(s,C3H), 5.57(d,J=10 Hz, C22H), 5.95(m,C23H).

EXAMPLE 28

24-Demethyl-25-de(2-butyl)-25-cyclohexylavermectin B1a and 24-Demethyl-25-de (2-butyl)-25-epicyclohexylavernectin B1a The Wittig reaction from 204 mg of (R,S)-[(3-cyclohexyl-3-trimethylsilyloxy)propyl]triphenylphosphonium iodide and 297 mg of aldehyde VIIA gave 130 mg of adduct. Cyclization of 116 mg of the adduct gave 35 mg of C25-normal and 40 mg of slower eluting C25-epi product (from PLC in 15% ethyl acetate-hexane). Desilylation of the individual compounds gave 13 mg of the normal C25 product (NMR (select signals) δ0.85(q,J=11 Hz), 1.03(br t, J=11 Hz), 4.08(s), 5.40(s, C3H and C1"H), 5.43(m, C19H), 5.59(d,J=10 Hz, C22H), 5.99(m,C23H)) and 15 mg of the 25-epi product (NMR (select signals) δ0.90(q,J=11 Hz), 1.03(m), 4.10(dt, C25H), 5.28(m, C19H), 5.38(d,J=3 Hz, C1"H), 5.44(s, C3H), 5.56(d,J=10 Hz, C22H), 5.93 (m, C23H)) with both mass spec FAB of 891 (M+Li).

EXAMPLE 29

24-Demethyl-25-de(2-butyl)-22,23-dihydro-22-hydroxyavermectin B1a

Commercially available 1-bromo-3-propanol was silylated with t-butyldimethylsilyl chloride in DMF with imidazole catalysis and the silylether was converted to a 0.5M grignard solution in THF by refluxing with magnesium chips overnight. To a solution of 140 mg of aldehyde VI in 4 mL of THF under argon at 0° C. was added 2 mL of the previously described Grignard reagent. After 20 min the reaction was quenched by the addition of 1 mL of 2N HCl, water, and ether. The ether extract was dried and evaporated to afford 186 mg of product which was treated with HF-pyridine-THF to remove all silyl groups. The product from the desilylation reaction (34 mg) was dissolved in 1 mL of dichloromethane and stirred with 18 mg of PPTS overnight at 20° C. PLC of this mixture gave a faster eluting product band which was characterized as the title compound by NMR (select signals) δ0.95(t,J=7 Hz), 1.01(d,J=6 Hz), 1.17(d,J=7 Hz), 1.88(s), 3.42(s), 3.44(s), 4.30(t,d,Jt=6 Hz, Jd=12 Hz), 4.77(d,J=3 Hz), 4.96(m), 5.32(m), 5.39(d,J=3 Hz), 5.42(s), 5.7–5.9(m) and mass spectra (EI, 802=M-$H_2O$).

EXAMPLE 30

22-Hydroxy-23-oxo-avermectin B2a

To 46 mg of 4",5-di-O-t-butyldimethylsilyl-7-O-trimethylsilyl-22-hydroxy-23-oxo-avermectin B2a in a polyethylene vial was added 3 mL of HF-pyridine-THF. After 22 h at room temperature, the usual aqueous work up and purification of the product by PLC gave 15 mg of title compound: NMR (select signals) δ1.0(m), 1.16(d,J=7 Hz), 1.49(s), 1.88(s), 3.16(t,J=9 Hz), 3.24(t,J=9 Hz), 3.41(s), 3.42(s), 3.96(m, 3H), 4.29(t,J=7 Hz), 4.67(s, 2H), 4.74(d,J=3 Hz), 4.90(d,J=8 Hz), 5.31(m), 5.38(d,J=3 Hz), 5.44(s), 5.7–5.9(m, 3H) and mass spec FAB 911 (M+Li).

EXAMPLE 31

22,23-Dihydro-24-demethyl-25-de(2-butyl)-25-cyclopentylavermectin B1a

A solution of 31 mg of 4",5-di-O-t-butyldimethylsilyl-7-O-trimethylsilyl-24-demethyl -25-de(2-butyl)-25-cyclopentylavermectin B1(Example 26) in 2 mL of distilled benzene and 17 mg of tris(triphenylphosphine)rhodium (I) chloride was stirred under an atmosphere of hydrogen in a sealed flask at room temperature and the reaction was followed by reverse phase HPLC. After 25 h the hydrogenation was complete to afford one product (21 mg) isolated by PLC on a 0.5 mm silica gel plate. The 21 mg of product was desilylated in 2 mL of HF-pyridine-THF to afford 9 mg of 22,23-dihydro-24-demethyl-25-de(2-butyl)-25-cyclopentylavermectin B1a, which was characterized by its mass and NMR spectra.

EXAMPLE 32

22,23-Dihydro-24-demethyl-25-de(2-butyl)-25-epicyclopentylavermectin B1a

Following the previously outlined procedure 36 mg of 4",5-di-O-t-butyldimethylsilyl-7 -O-timethylsilyl-24-demethyl-25-de(2-butyl)-25-epicyclopentylavermectin B1(Example 26) was hydrogenated with 17 mg of Wilkinson's catalyst after 44 h to afford 26 mg of 4",5-di-O-t-butyldimethylsilyl-7-O-trimethylsilyl-22,23-dihydro-24-demethyl-25-de(2-butyl)-25-epicyclopentylavermectin B1. Treatment of this with 2 mL of HF-pyridine-THF for 3 days afforded 10 mg of desilylated product. NMR (select signals) δ0.84(q,J=12 Hz), 1.49(s), 1.6(m), 1.87(s), 3.42(s), 3.43(s), 3.95(s), 3.96(d,J=6 Hz), 4.2(s), 4.3(t,J=6 Hz), 4.68(AB,J=12 Hz), 4.8(d,J=3 Hz), 5.0(d,J=12 Hz), 5.40(s,d), 5.44(m), 5.7–5.9(m,3H); mass spec FAB 879 (M+Li).

EXAMPLE 33

(R,S)-[(2-Phenyl-3-trimethylsilyloxy)propyl] triphenylphosphonium iodide

To 5.11 g of phenylmalonic acid in 50 mL of ether cooled to 0° C. was added 60 mL of a 1M solution of lithium aluminum hydride in THF. After stirring the mixture at room temperature overnight, the excess lithium aluminum hydride was quenched with ethyl acetate and dilute hydrochloric acid. The 1,3-dihydroxy-2-phenylpropane was isolated by ether extraction, and subsequent purification by flash chromatography gave 1.34 g of product characterized by NMR. This is treated with one equivalent of tosyl chloride in pyridine to afford the monotosylate. The purified monotosylate is heated in acetone with excess sodium iodide (as described in Example 23) to produce the 1-iodo-2-phenyl-3-propanol. Subsequent silylation with trimethylsilyltriflate (as in Example 16) and treatment of the iodosilylether with triphenylphosphine in toluene at 100 ° C. gives the title compound, which is characterized by its NMR and mass spectra.

EXAMPLE 34

(R,S)-[(2-alkyl(aryl)(alkoxy)-3-trimethylsilyloxy) propyl]triphenylphosphonium iodide Reduction of the appropriate alkyl, aryl, or alkoxy malonic acids and their corresponding lower alkyl esters or 2,2-disubstituted alkyl(aryl) malonic acids and their corresponding lower alkyl esters provides the starting 2-alkyl (aryl)(alkoxy)- 1,3-propanediols or 2,2-di -alkyl(aryl)-1,3-propanediols which are converted to the following phosphonium salts by the procedure outlined in Example 33:

(R,S)-[(2-ethyl-3-trimethylsilyloxy)propyl] triphenylphosphonium iodide;

(R,S)-[(2-benzyl-3-trimethylsilyloxy)propyl] triphenylphosphonium iodide;

(R,S)-[(2-cyclohexyl-3-trimethylsilyloxy)propyl] triphenylphosphonium iodide;

(R,S)-[(2-(3-thiophenyl)-3-trimethylsilyloxy)propyl] triphenylphosphonium iodide;

(R,S)-[(2-ethoxy-3-trimethylsilyloxy)propyl] triphenylphosphonium iodide;

(R,S)-[(2-(1 -butyl)-3-trimethylsilyloxy)propyl] triphenylphosphonium iodide;

(R,S)-[(2-allyl-3-trimethylsilyloxy)propyl] triphenylphosphonium iodide;

(R,S)-[(2-(2-cyclopentenyl)-3-trimethylsilyloxy)propyl] triphenylphosphonium iodide;

(R,S)-[(2-(2-octadecyl)-3-trimethylsilyloxy)propyl] ttriphenylphosphonium iodide;

(R,S)-[(2-ethoxy-3-trimethylsilyloxy)propyl] triphenylphosphonium iodide;

[(2,2-dimethyl-3-trimethylsilyloxy)propyl] triphenylphosphonium iodide.

EXAMPLE 35

Preparation of 3-chloro-2-ethyl-1-alkyl(aryl)-1-propanols and 3-chloro-2-methyl-1-alkyl(aryl)- 1-propanols 2-Ethylacrolein (39 g) was chilled to 0° C. in a flask and dry HCl gas was bubbled in until 17 g (1 equiv.) was absorbed. The mixture was then immediately distilled at reduced pressure to afford 9.7 g of 2-ethyl-3-chloropropanal (b.p. 47° C./14 torr). This was added to an excess of the appropriate Grignard reagent in ether at room temperature as described in Example 18 or to an alkyl(aryl)lithium at −78° C. to produce the corresponding 3-chloro-2-ethyl-1-alkyl (aryl)-1-propanol:

3-chloro-2-ethyl-1-phenyl-1-propanol;

3-chloro-2-ethyl-1-cyclopentyl-1-propanol;

3-chloro-2-ethyl-1-(3,5-dichlorophenyl)-1-propanol.

Additionally, reduction of the 2-ethyl-3-chloropropanal with sodium borohydride in methanol provides the 2-ethyl-3-chloro-1-propanol.

In similar fashion the hydrochlorination of 2-methylacrolein and subsequent reaction with a Grignard reagent or alkyl(aryl)lithium produce the 3-chloro-2-methyl-1-alkyl(aryl)-1-propanols:
3-chloro-2-methyl- 1-(4-methoxyphenyl)-1-propanol;
3-chloro-2-methyl-1-(3,5-dichlorophenyl)-1-propanol;
3-chloro-2-methyl-1-(4-acetylaminophenyl)-1-propanol;
3-chloro-2-methyl-1-benzyl- 1-propanol; 3-chloro-2-methyl-1-phenyl- 1-propanol.

EXAMPLE 36

[(2-Ethyl-3-alkyl(aryl)-3-trimethylsilyloxy)propyl] triphenylphosphonium iodide and [(2-Methyl-3-alkyl(aryl)-3-trimethylsilyloxy)propyl] triphenylphosphonium iodide Following the process given in Examples 15–17, the chloropropanols described in Example 35 are converted to their corresponding phosphonium iodides:
[(2-methyl-3-(4-methoxyphenyl)-3-trimethylsilyloxy) propyl]triphenylphosphonium iodide;
[(2-methyl-3-(3,5-dichlorophenyl)-3-trimethylsilyloxy) propyl]triphenylphosphonium iodide;
[(2-methyl-3-(4-acetylaminophenyl)-3-trimethylsilyloxy) propyl]triphenylphosphonium iodide;
[(2-methyl-3-benzyl-3-trimethylsilyloxy)propyl] triphenylphosphonium iodide;
[(2-methyl-3-phenyl-3-trimethylsilyloxy)propyl] triphenylphosphonium iodide;
[(2-ethyl-3-(4-methoxyphenyl)-3-trimethylsilyloxy)propyl] triphenylphosphonium iodide;
[(2-ethyl-3-phenyl-3-trimethylsilyloxy)propyl] triphenylphosphonium iodide;
[(2-ethyl-3-(3,5-dichlorophenyl)-3-trimethylsilyloxy) propyl]triphenylphosphonium iodide;
[(2-ethyl-3-benzyl-3-trimethylsilyloxy)propyl] triphenylphosphonium iodide;
[(2-ethyl-3-trimethylsilyloxy)propyl]triphenylphosphonium iodide.

EXAMPLE 37

24-Demethyl-25-de(2-butyl)-25-(alkyl(aryl)) avermectin B 1 a and 24-Demethyl-25-de(2-butyl)-25-epi-(alkyl(aryl))avermectin B1a Following the procedure given by Examples 7–9 utilizing
(R,S)-[(3-(benzyl)-3-trimethylsilyloxy)propyl] triphenylphosphonium iodide;
(R,S)-[(3-(2-thienyl)-3-trimethylsilyloxy)propyl] triphenylphosphonium iodide;
(R,S)-[(3-(4-pyridyl)-3-trimethylsilyloxy)propyl] triphenylphosphonium iodide;
(R,S)-[(3-(1-octyl)-3-trimethylsilyloxy)propyl] triphenylphosphonium iodide;
(R,S)-[(3-(1-ethyl)-3-trimethylsilyloxy)propyl] triphenylphosphonium iodide (Example 19);
(R) or (S)-[(3-trimethylsilyloxy)butyl] triphenylphosphonium iodide (Example 20) and aldehydes VIIA or VIIB, the corresponding 24-demethyl-25-de(2-butyl)-25-(benzyl)avermectin B1a,
24-demethyl-25-de(2-butyl)-25-(2-thienyl)avermectin B1a,
24-demethyl-25-de(2-butyl)-25-(4-pyridyl)avermectin B1a,
24-demethyl-25-de(2-butyl)-25-(octyl)avermectin B1a,
24-demethyl-25-de(2-butyl)-25-(ethyl)avermectin B1a,
24-demethyl-25-de(2-butyl)-25-(methyl)avermectin B1a,
and their respective 25-epi isomers are obtained and characterized by their NMR and mass spectra.

EXAMPLE 38

25-De(2-butyl)-25-alkyl(aryl)avermectin B1a and 25-De(2-butyl)-25-epialkyl(aryl)avermectin B1a The Wittig condensations of
[(2-methyl-3-(4-methoxyphenyl)-3-trimethylsilyloxy) propyl]triphenylphosphonium iodide;
[(2-methyl-3-(3,5-dichlorophenyl)-3-trimethylsilyloxy) propyl]triphenylphosphonium iodide;
[(2-methyl-3-(4-acetylaminophenyl)-3-trimethylsilyloxy) propyl]triphenylphosphonium iodide;
[(2-methyl-3-benzyl-3-trimethylsilyloxy)propyl] triphenylphosphonium iodide; and [(2-methyl-3-phenyl-3-trimethylsilyloxy)propyl]triphenylphosphonium iodide (Example 36);
[(2-methyl-3-trimethylsilyloxy)butyl] triphenylphosphonium iodide (Example 21); and
[(2-methyl-3-trimethylsilyloxy)pentyl] triphenylphosphonium iodide (Example 22) with either aldehyde VIIA or VIIB and subsequent cyclization and desilylation provide respectively:
25-de(2-butyl)-25-(4-methoxyphenyl)avermectin B1a;
25-de(2-butyl)-25-(3,5-dichlorophenyl)avermectin B1a;
25-de(2-butyl)-25-(4-acetylaminophenyl)avermectin B1a;
25-de(2-butyl)-25-benzylavermectin B1a;
25-de(2-butyl)-25-phenylavermectin B1a;
25-de(2-butyl)-25-methylavermectin B1a;
25-de(2-butyl)-25-ethylavermectin B1a and their corresponding C25-epimers, which are characterized by their NMR and mass spectra.

EXAMPLE 39

24-Demethyl-24-ethyl-25-de(2-butyl)-25-alkyl (aryl) avermectin B1a and 24-Demethyl -24-ethyl-25-de (2-butyl)-25-epi-alkyl(aryl)avenmectin B1a The Wittig condensation of
[(2-ethyl-3-(4-methoxyphenyl)-3-trimethylsilyloxy)propyl] triphenylphosphonium iodide;
[(2-ethyl-3-phenyl-3-trimethylsilyloxy)propyl] triphenylphosphonium iodide;
[(2-ethyl-3-(3,5-dichlorophenyl)-3-trimethylsilyloxy) propyl]triphenylphosphonium iodide;
[(2-ethyl-3-benzyl-3-trimethylsilyloxy)propyl] triphenylphosphonium iodide; and [(2-ethyl-3-trimethylsilyloxy)propyl]triphenylphosphonium iodide with aldehyde VIIA or VIIB following the procedure of Examples 7–9 gives after desilylation:
24-demethyl-24-ethyl-25-de(2-butyl)-25-(4-methoxyphenyl)avermectin B1a;
24-demethyl-24-ethyl-25-de(2-butyl)-25-phenylavermectin B1a;
24-demethyl-24-ethyl-25-de(2-butyl)-25-(3,5-dichlorophenyl)avermectin B1a;
24-demethyl-24-ethyl-25-de(2-butyl)-25-benzylavermectin B1a;
24-demethyl-24-ethyl-25-de(2-butyl)-avermectin B1a and their corresponding C24,C25 diastereomers characterized by NMR and mass spectra.

EXAMPLE 40

24-Demethyl-24-ethoxy-25-de(2-butyl)aver—ectin B1a and 24-Methyl-25-de(2-butyl)avermectin B1a Following the process given by Examples 7–9, (R,S)-[(2-ethoxy-3-trimethylsilyloxy)propyl]triphenylphosphonium iodide and [(2,2-dimethyl-3-trimethylsilyloxy)propyl] triphenylphosphonium iodide are condensed via the Wittig reaction with aldehydes VIIA or VIIB to give adducts VIIIA or VIIIB which is cyclized and desilylated to give the title compounds IX (Scheme 3), which are characterized by their NMR and mass spectra.

EXAMPLE 41

5-O-t-Butyldimethylsilyl- 13-deoxy-avenmectin B2a aglycone

To a solution of 10 g of 13-deoxy-avermectin B2a aglycone in 80 mL of dimethylformamide and 6 mL of triethylamine is added a solution of 2 g of t-butyldimethylsilyl chloride in 40 mL of dichloromethane. The mixture is stirred at room temperature for 16 h then poured into ice water and extracted with dichloromethane. The extracts are combined and evaporated to give a glassy solid which is flash chromatographed to give the title compound characterized by its NMR and mass spectra.

EXAMPLE 42

5-O-t-Butyldimethylsilyl-13-deoxy-23-oxo-avermectin B2a aglycone

To a solution of 10 mL of dichloromethane and 0.25 mL of dimethyl sulfoxide at −78° C. is added 0.16 mL of oxalyl chloride. A solution of 1 g of 5-O-t-butyldimethylsilyl-13-deoxy-avermectin B2a aglycone in 4 mL of dichloromethane is added dropwise while keeping the temperature below −70° C. The mixture is stirred at −78° C. for 1 h before 0.11 mL of triethylamine is added dropwise. After 1 h at 10° C., the reaction is worked up with water and chromatographic purification of the extracted product affords 5-O-t -butyldimethylsilyl-13-deoxy-23-oxo-avermectin B2a aglycone characterized by its NMR and mass spectra.

EXAMPLE 43

5-O-t-Butyldimethylsilyl- 13-deoxy-7,23-di-O-trimethylsilyl-22,23-dehydroavermectin B2a aglycone To a solution of 200 mg of 5-O-t-butyldimethylsilyl-13-deoxy-23-oxo-avermectin B2a aglycone in 4 mL of THF at −78° C. is added 0.6 mL of a 1.0M solution of lithium bis(trimethylsilyl)amide in hexanes. The mixture is stirred at −78° C. for 1 h before 0.20 mL of the supernatant of a centrifuged 1:3 mixture of triethylamine and trimethylchlorosilane is added dropwise. After another 30 min, 2 mL of a saturated solution of sodium bicarbonate is added and the mixture is allowed to warm to room temperature. The mixture is extracted with ether and the extracts are combined, dried over magnesium sulfate, and concentrated to afford 5-O-t-butyldimethylsilyl-13-deoxy -7,23-di-O-trimethylsilyl-22,23-dehydroavermectin B2a aglycone characterized by its NMR spectrum.

EXAMPLE 44

5-O-t-Butyldimethylsilyl-13-deoxy-22-hydroxy-23-oxo-avermectin B2a aglycone

To a solution of 150 mg of 5-O-t-butyldimethylsilyl-13-deoxy-7,23-di-O-trimethylsilyl -22,23-dehydroavermectin B2a aglycone in 2 mL of dichloromethane is added a solution of 25 mg of m-chloroperbenzoic acid in 1 mL of dichloromethane. After 20 min 0.2 mL of dimethyl sulfide is added to react with the remaining peracid. After 30 min, 1 mL of a 1% acetic acid in methanol solution is added. The mixture is concentrated after an additional 30 min and PLC affords the title compound characterized by its NMR and mass spectra.

EXAMPLE 45

13-Deoxyaglycone-VI (Scheme 1: partial structure VI)

To a solution of 500 mg of 5-O-t-butyldimethylsilyl-13-deoxy-22-hydroxy-23-oxo-avermectin B2a aglycone in 6 mL of benzene is added 400 mg of lead tetraacetate in one portion with rapid stirring. After 30 min at room temperature the solution is poured into a separatory funnel containing 12 mL of water and 600 mg of sodium sulfite. The mixture is shaken and extracted with ethyl acetate. The combined extracts are dried, concentrated, and flash chromatographed to afford the title compound characterized by its NMR and mass spectra.

EXAMPLE 46

13-Deoxyaglycones VIIA and VIIB (Scheme 1: partial structures VIIA and VIIB)

To a solution of 800 mg of PPTS in 8 mL of dry methanol is added 1.5 g of 13-deoxy-VI aglycone. After 1.5 h at room temperature, 0.5 mL of triethylamine is added and the mixture is evaporated to dryness under vacuum. The residual solid is taken up in dichloromethane and flash chromatographic separation affords the title compounds characterized by their NMR and mass spectra.

EXAMPLE 47

24-Demethyl-25-de(2-butyl)-25-(3-furyl)-avermectin B1a and 24-Demethyl-25-de(2-butyl)-25-epi(3-furyl)avermectin B1a To a mixture of 150 mg of (R,S)-[(3-(3-furyl)-3-trimethylsilyloxy)propyl]triphenylphosphonium iodide in 1 mL of distilled toluene under argon is added 0.4 mL of a 0.5M solution of potassium bis(trimethylsilyl)amide. The mixture is stirred for 15 min at room temperature before cooling to −78° C. A solution of 200 mg of 13-deoxyaglycone VIIA in 0.5 mL of toluene is added and the mixture is allowed to warm to room temperature. The mixture is then quenched with a sodium bicarbonate solution and PLC separation of the mixture affords 5-O-t-butyldimethylsilyl -7-O-trimethylsilyl- 13-deoxy-21,21-O-, 22,23-bis- seco-21 -methoxy-24-demethyl-25-de(2-butyl)-25-(3-furyl)-25-O-trimethylsilylavermectin B1a aglycone and its C25 epimer. This is cyclized and desilylated as in Examples 8 and 9 to give the title compounds characterized by their NMR and mass spectra.

EXAMPLE 48

24-Demethyl-25-de(2-butyl)-25-phenylavermectin B1a monosacccharide and aglycone

A mixture of 4.6 ml of water, 4.6 ml of concentrated sulfuric acid, and 17 ml of tetrahydrofuran is added over 30 minutes to a solution of 2.22 g of 24-demethyl-25-de(2-butyl)-25-phenylavermectin B1a in 20 ml of tetrahydrofuran stirred in an ice bath. Then the reaction mixture is stirred 24 hours at room temperature. Addition of 30 ml of ice water, extraction with methylene chloride, washing with aqueous NaHCO$_3$ solution and water, drying and concentration in vacuo gives a brown foam. Purification and separation by silicagel column chromatography using methylene chloride/ethyl acetate solvent mixtures affords pure 24-demethyl-25-de(2-butyl)-25-phenylavermectin B1a monosaccccharide and 24-demethyl-25-de(2-butyl)-25-phenylavermectin B1a aglycone which are characterized by their mass and NMR spectra.

EXAMPLE 49

24-Demethyl-25-de(2-butyl)-22,23-dihydro-25-phenylavermectin B1a

A solution of 2.65 g of 24-demethyl-25-de(2-butyl)-25-phenylavermectin B1a and 1.0 g of Wilkinson's homogeneous hydrogenation catalyst tris(triphenylphosphine) rhodium(I) chloride in 160 ml of benzene is shaken at 25° C. under an atmosphere of hydrogen pressurized to 15 lbs for 20 hours, when one equivalent of hydrogen is absorbed. Evaporation of the solvent gives a brown glass, which is purified by through silicagel column chromatography with methylene chloride/ethyl acetate solvent mixtures to afford pure 24-demethyl-25-de(2-butyl)-22,23-dihydro-25-phenylavermectin B1a, which is characterized by its mass and NMR spectra.

EXAMPLE 50

24-Demethyl-25-de(2-butyl)-22,23-dihydro-25-phenylavermectin B1a aglycone

To a stirred mixture of 20 ml of 99:1 methanol-concentrated sulfuric acid 2.0 g of 24-demethyl-25-de(2-butyl)-22,23-dihydro-25-phenylavermectin B1a is added and stirred at room temperature for 18 hours. Then it is neutralized by the addition of saturated aqueous NaHCO$_3$ solution, diluted with ether and enough water to obtain two layers and complete solution, and the ether layer is separated. The aqueous phase is extracted with two additional portions of ether, the combined organic phases are washed with water and brine, dried and concentrated to a light foam. Purification by silicagel column chromatography with methylene chloride/ethyl acetate solvent mixtures gives pure 24-demethyl-25-de(2-butyl)-22,23-dihydro-25-phenylavermectin B1a aglycone, which is characterized by its mass and NMR spectra.

EXAMPLE 51

5-O-tert-Butyldimethylsilyl-24-demethyl-25-de(2-butyl)-22,23-dihydro-25-phenylavermectin B1a aglycone A solution of 1.0 g of 24-demethyl-25-de(2-butyl)-22,23-dihydro-25-phenylavermectin B1a aglycone in 20 ml of dimethylformamide is stirred at room temperature under N$_2$. Sequentially 0.6 g of imidazole followed by 0.75 g of tert-butyldimethylsilyl chloride are added. After 40 minutes the reaction mixture is poured onto 150 ml of water and extracted with methylene chloride. The extract is washed with water, dried and concentration in vacuo to a thick oil. This is purified by chromatography on a column of 30 g of silicagel with CH$_2$C$_2$ -1$_2$-EtOAc solvent mixture to give 5-O-tert -butyldimethylsilyl-24-demethyl-25-de(2-butyl)-22,23-dihydro-25-phenylavermectin B1a aglycone, which is characterized by its mass and NMR spectra.

EXAMPLE 52

5-O-tert-Butyldimethylsilyl- 13-chloro-24-demethyl-25-de(2-butyl)-22,23-dihydro-25-phenylavermectin B1a aglycone A solution of 500 mg of 5-O-tert-butyldimethylsilyl-24-demethyl-25-de(2-butyl)-22,23-dihydro-25-phenylavermectin B1a aglycone, 0.75 ml (600 mg) of N,N-diisopropylethylamine, and 750 mg of 4-dimethylaminopyridine is stirred at room temperature under N$_2$. To this a solution of 800 mg of 2-nitrobenzenesulfonyl chloride in 10 ml of CH$_2$Cl$_2$ is added dropwise during 10 minutes and the reaction mixture is stirred at room temperature for 2 hours. Then it is poured onto 200 ml of water and extracted with ether. The extract is washed with water, dried and concentrated in vacuo to a light foam. Purification on several 1000 micron thick silicagel layer chromatography plates gives pure 5-O-tert-butyldimethylsilyl- 13-chloro-24-demethyl-25-de(2-butyl)-22,23-dihydro-25-phenylavermectin B1a aglycone, which is characterized by its mass and NMR spectra.

EXAMPLE 53

5-O-tert-Butyldimethylsilyl-13-deoxy-24-demethyl-25-de(2-butyl)-22,23-dihydro-25-phenylavermectin B1a aglycone.

A solution of 260 mg of 5-O-tert-butyldimethylsilyl-13-chloro-24-demethyl-25-de(2-butyl)-22,23-dihydro-25-phenylavermectin B1a aglycone and 35 mg of 2,2'-azobis(2-methylpropionitrile) in 5 ml of dry toluene is stirred in an oil bath maintained at 80° to 85° C. under N$_2$. Through a syringe 1.0 ml of tri-n-butyltin hydride is added rapidly. After heating for 4 hours the mixture is concentrated in high vacuum to a residue of about 2 ml. This is diluted with CH$_2$Cl$_2$ and purified on a column containing 15 g of silicagel with CH$_2$Cl$_2$-EtOAc as solvent to give 5-O-tert-butyldimethylsilyl-13-deoxy-24-demethyl -25-de(2-butyl)-22,23-dihydro-25-phenylavermectin B1a aglycone, which is characterized by its mass and NMR spectra.

EXAMPLE 54

13-Deoxy-24-demethyl-25-de(2-butyl)-22,23-dihydro-25-phenylavermectin B1a aglycone A solution containing 170 mg of 5-O-tert-butyldimethylsilyl- 13-deoxy-24-demethyl-25-de(2-butyl)-22,23-dihydro-25-phenylavermectin B1a aglycone and 170 mg of p-toluenesulfonic acid monohydrate in 17 ml of methanol is treated as fully described in Example 56 to give 13-deoxy-24-demethyl-25-de(2-butyl)-22,23-dihydro-25-phenylavermectin B1a aglycone, which is characterized by its mass and NMR spectra.

EXAMPLE 55

5-O-tert-Butyldimethylsilyl- 13-fluoro-24-demethyl-25-de(2-butyl)-22,23-dihydro-25-phenylavermectin B1a aglycone A solution of 0.2 ml of diethylaminosulfur trifluoride in 8 ml of CH$_2$Cl$_2$ is stirred at −65° C. under N$_2$. To this is added dropwise a solution of 1 g of 5-O-tert-butyldimethylsilyl -24-demethyl-25-de(2-butyl)-22,23-dihydro-25-phenylavermectin B1a aglycone in 8 ml of CH$_2$Cl$_2$ during 15 minutes. The reaction mixture is stirred for 30 minutes at −65 ° C. and for 1 hour at −20 ° C. and then allowed to come to room temperature during 1.5 hours. The reaction mixture is then poured into dilute aqueous NaHCO$_3$ solution, extracted with CH$_2$Cl$_2$, washed with water, dried, and concentrated in vacuo to a light glass. Purification by preparative silica gel layer chromatography with hexane-EtOAc solvent mixtures gives a mixture of 5-O-tert-butyldimethylsilyl-13-alpha- and 13-beta-fluoro-24- demethyl-25-de(2-butyl)-22,23-dihydro-25-phenylavermectin B1a aglycones, which is characterized by its mass and NMR spectra.

EXAMPLE 56

13-Fluoro-24-demethyl-25-de(2-butyl)-22,23-dihydro-25-phenylavermectin B1a aglycone A solution of 130 mg of a mixture of 5-O-tert-butyldimethylsilyl-13-alpha- and 13-beta -fluoro-24-demethyl-25-de(2-butyl)-22,23-dihydro-25-phenylavermectin B1a aglycones 12 ml of methanol containing 120 mg of p-toluenesulfonic acid monohydrate is kept at room temperature for 30 to 45 minutes, when dilute aqueous $NaHCO_3$ solution is added. The product is extracted with EtOAc, isolated and purified as descibed in Example 54 to give a mixture of 13-alpha- and 13-beta-fluoro-24-demethyl-25-de(2-butyl)-22,23-dihydro-25-phenylavermectin B1a aglycones, which is characterized by its mass and NMR spectra.

EXAMPLE 57

5-O-t-Butyldimethylsilyl-24-demethyl-25-de(2-butyl)-25-cyclopentylavermectin B1a A solution of 50 g of 24-demethyl-25-de(2-butyl)-25-cyclopentylavermectin B1a, 24 g of imidazole and 24 g of tert-butyldimethylsilyl chloride in 400 ml of anhydrous dimethylformamide is stirred at room temperature for 50 minutes. The reaction mixture is poured into 1.5 l of ice cold water and the aqueous phase is extracted four times with 200 ml of ether. The organic phase is washed twice with water, aqueous sodium chloride solution, dried with magnesium sulfate and concentrated in vacuo to a white foam. The crude product is purified by silica gel column chromatography with a methylene chloride-ethyl acetate-90:10 to 70:30 solvent system to give 5-O-t-butyldimethylsilyl-24-demethyl-25-de(2-butyl)-25-cyclopentylavermectin B1a as an amorphous foam, which is characterized by its $^1$H-NMR- and mass spectra.

EXAMPLE 58

5-O-t-Butyldimethylsilyl-4"-oxo-24-demethyl-25-de(2-butyl)-25-cyclopentylavermectin B1a To a solution containing 9.1 ml of oxalyl chloride in 230 ml of dry methylene chloride stirred at −60° C. is added 15 ml of dry dimethylsulfoxide dissolved in 120 ml of dry methylene chloride during 15 min. Then a solution of 46.5 g of 5-O-t-butyldimethylsilyl -24-demethyl-25-de(2-butyl)-25-cyclopentylavermectin B1a dissolved in 230 ml of dry methylene chloride is added over a period of 15 minutes while maintaining the temperature at −60° C. The reaction mixture is stirred at this temperature for 30 minutes when 65 ml of dry triethylamine is added. The mixture is stirred for 5 additional minutes at −60° C., and then the cooling bath is removed and the reaction mixture is allowed to come to ambient temperature. After addition of water the reaction product is extraxted with methylene chloride, the extract is washed with water, dried and concentrated in vacuo to a yellow foam. This is identified by its mass and NMR spectra as 5-O-t -butyldimethylsilyl-4"-oxo-24-demethyl-25-de(2-butyl)-25-cyclopentylavermectin B1a, which is used for further chemical reactions without purification.

EXAMPLE 59

4"-epi-Amino-5-O-t-butyldimethylsilyl-4"-deoxy-24-demethyl-25-de(2-butyl)-25-cyclopentylavermectin B1a For the reductive amination 12 mg of sodium cyanoborohydride is added to a solution of 200 mg of 5-O-t-butyldimethylsilyl-4"-oxo-24-demethyl-25-de(2-butyl)-25-cyclopentylavermectin B1a (from Example 58) and 160 mg of ammonium acetate in 3 ml of methanol, and the reaction mixture is stirred at room temperature for 1 hour. Then it is poured into aqueous $Na_2CO_3$ solution, and the organic products are extracted with ethyl acetate. The extract is washed with water, dried, and concentrated in vacuo to a yellow oil. Preparative silica gel layer chromatography with 98:2 methylene chloride-methanol solvent gives 4"-epi-amino-5-O-t-butyldimethylsilyl-4"-deoxy-24-demethyl-25-de(2-butyl)-25-cyclopentylavermectin B1a, and 4"-amino-5-O-t-butyldimethylsilyl-4"-deoxy -24-demethyl-25-de(2-butyl)-25-cyclopentylavermectin B1a as light foams, which are characterized by their mass and their NMR spectra.

EXAMPLE 60

4"-epi-Amino-4"-deoxy-24-demethyl-25-de(2-butyl)-25-cyclopentylavermectin B1a

A solution of 100 mg of 4"-epi-amino-5-O-t-butyldimethylsilyl-4"-deoxy-24-demethyl -25-de(2-butyl)-25-cyclopentylavermectin B1a (from example 59) in 10 ml of methanol containing 1 % of p-toluenesulfonic acid monohydrate is kept at room temperature for 30 minutes and then poured into aqueous $NaHCO_3$ solution. The product is isolated by extraction with ethyl acetate, and obtained in pure form after preparative silica gel layer chromatography as a light yellow foam, which is characterized by its mass and NMR spectra as 4"-epi-amino-4"-deoxy-24-demethyl-25-de(2-butyl)-25-cyclopentylavermectin B1a.

EXAMPLE 61

4"-epi-Acetylamino-4"-deoxy-24-demethyl-25-de(2-butyl)-25-cyclopentylavermectin B1a A solution of 50 mg of 4"-epi-amino-4"-deoxy-24-demethyl-25-de(2-butyl)-25-cyclopentylavermectin B1a in 0.5 ml of methylene chloride is treated with 0.007 ml of acetic anhydride at room temperature for 1 hour. The reaction mixture is then diluted with ethyl acetate and washed with dilute $NaHCO_3$ solution and water, and is dried and concentrated in vacuo to a white foam, which is characterized by its mass spectrum and $^1$H-NMR spectrum as 4"-epi-acetylamino-4"-deoxy-24-demethyl-25-de(2-butyl)-25-cyclopentylavermectin B1a.

EXAMPLE 62

5-O-t-Butyldimethylsilyl-4"-deoxy-4"-epi-methylamino-24-demethyl-25-de(2-butyl)-25-cyclopentylavermectin B1a A solution of 26 ml of glacial acetic acid in 300 ml of MeOH is treated with methylamine gas at 0° C. until the pH of the solution reached 9.0. To this a solution containing 44.5 g of 5-O-t-butyldimethylsilyl-24-demethyl-25-de(2-butyl)-25-cyclopentyl-4"-oxoavermectin B1a in 200 ml of methinol is added, and the reaction mixture is stirred at room temperature for 1 hour, when a solution of 3.5 g of sodiumcyanoborohydride in 75 ml of MeOH is added dropwise over 10 min. After 50 min the reaction mixture is poured into 1.5 of cold aqueous $Na_2CO_3$ solution and the product is extracted with ether. The extract is washed with water, dried, and concentrated in vacuo to a yellow foam. Thin layer chromatography (silica gel, methylene chloride-ethyl acetate 85:15 ) of the crude product at this point shows several spots. Further purification by silica gel column chromatography using methylene chloride-ethyl acetate solvent mixtures gives under others 5-O-tert-butyldimethylsilyl-4"-deoxy-4"-epi-methylamino-24-demethyl-25-de(2-butyl)-25-cyclopentylavermectin B1a as a light foam, which is characterized by its mass and NMR spectra.

EXAMPLE 63

4"-Deoxy-4"-epi-methylamino-24-demethyl-25-de(2-butyl)-25-cyclo2pentylavermectin B1a A solution of 14 g of 5-O-tert-butyldiinethylsilyl-4"-deoxy-4"-epi-methylamino-24-demethyl-25-de(2-butyl)-25-cyclopentylavermectin B1a in 200 ml of methanol and a solution of 7 g of p-toluenesulfonic acid monohydrate in 500 ml of methanol is mixed and stirred at room temperature for 45 minutes, and then poured into dilute aqueous $Na_2CO_3$ solution. The product is extracted with ethyl acetate, washed with water and dried over $MgSO_4$, concentrated in vacuo, and purified by preparative silicagel column chromatography with a methylene chloride-methanol 95:5 solvent mixture to give 4"-deoxy-4"-epi-methylamino-24-demethyl-25-de(2-butyl)-25-cyclopentylavermectin B1a, which is identified by NMR and mass spectra.

EXAMPLE 64

5-O-tert-Butyldimethylsilyl-24-demethyl-25-de(2-butyl)- 13-O-(2-methoxyethoxy)methyl-22,23-dihydro-25-phenylavermectin B1a aglycone 2-(Methoxyethoxy)methyl chloride (360 microliter) is added dropwise at room temperature to a stirred solution containing 200 mg of 5-O-tert-butyldimethylsilyl-24-demethyl-25-de(2-butyl)-22,23-dihydro-25-phenylavermectin B1a aglycone (obtained in Example 4) and 650 microliter of N,N-diisopropylethylamine in 0.8 ml of methylene chloride under $N_2$. After 20 hours it is diluted with methylene chloride, washed with water, dried, and concentrated in vacuo to a light glass. Purification by preparative silica gel layer chromatography using methylene chloride containing 0.5 to 5% of methanol as solvent gives 5-O-tert-butyldimethylsilyl-24-demethyl-25-de(2-butyl)-13-O-(2-methoxyethoxy)methyl-22,23-dihydro-25-phenylavermectin B1a aglycone, which is characterized by its mass and NMR spectra.

What is claimed is:

1. A compound which is:
   24-demethyl-25-de(2-butyl)avermectin B1a;
   24-demethyl-25-de(2-butyl)-22,23-dihydroavermectin B1a;
   24-demethyl-25-de(2-butyl)-25-phenylatvcrmectin B1a;
   24-demethylavermectin B1a;
   24-demethyl-25-de(2-butyl)-25-cyclopentylavermectin B1a;
   4"-deoxy-4"-epi-acetylamino-24-demethylavermectin B1a or
   24-demethyl-25-de(2-butyl)-13-deoxy-25-phenylavermectin B1a aglycone.

2. A method for the treatment of parasitic infections of animals, which comprises treating the infected animal with an effective amount of a compound of claim 1.

3. A composition useful for the treatment of animals or plants infected with parasites, which comprises an inert carrier and an effective amount of a compound of claim 1.

4. A method for the treatment of parasitic infections of plants which comprises treating the infected plant, or the soil in which the infected plant grows, with an effective amount of a compound of claim 1.

* * * * *